United States Patent

Bumstead et al.

Patent Number: 5,843,722
Date of Patent: *Dec. 1, 1998

[54] COCCIDIOSIS POULTRY VACCINE

[75] Inventors: Janene Marilyn Bumstead, Wantage; Paul Patrick James Dunn, Chalgrove; Fiona Margaret Tomley, Oxford, all of England; Arnoldus Nicolaas Vermeulen, Cuijk, Netherlands

[73] Assignee: Akzo Nobel N.V., Arnhem, Netherlands

[*] Notice: The term of this patent shall not extend beyond the expiration date of Pat. No. 5,795,741.

[21] Appl. No.: 668,416

[22] Filed: Jun. 21, 1996

Related U.S. Application Data

[63] Continuation of Ser. No. 338,057, Nov. 10, 1994.

[30] Foreign Application Priority Data

Nov. 12, 1993 [EP] European Pat. Off. ........... 93.3090789

[51] Int. Cl.$^6$ .................................................. A61K 39/002
[52] U.S. Cl. ................ 435/69.3; 435/172.3; 435/252.33; 435/258.4; 435/320.1; 536/23.1; 536/23.7; 424/191.1; 424/267.1; 424/271.1
[58] Field of Search ............................. 435/69.3, 252.33, 435/258.4, 320.1, 172.3; 424/191.1, 271.1, 267.1; 536/23.1, 23.7; 514/2

[56] References Cited

U.S. PATENT DOCUMENTS 5,387,414 2/1995 Harwood et al. ..................... 424/191.1
5,403,581 4/1995 Binger etal. ......................... 424/191.1

FOREIGN PATENT DOCUMENTS 0 552 482 1/1993 European Pat. Off. .

OTHER PUBLICATIONS

Lillehoj et al., "Protection Against Eimeria Acervuline Infection Correlates with the T–Cell Response to the Recombinant Surface Merozite Antigen P150,", *FASEB J.*, vol. 2, No. 4, 1988, p. A881.

Lillehoj, H.S., "Immune Response During Coccidiosis in SC and FP Chickens. I. In–Vitro Assessment of T–Cell Proliferation Response to Stage–specific Parasite Antigens," *Veterinary Immunology and Immunopathology*, vol. 13, No. 4, Dec. 1986, p. 321–330.

Lillehoj, H.S., "Interaction of Helper T–Cells and Cytotoxic T–Cells is Necessary for Protection Against Eimeria Tenella and E. Maxima Infections in Chickens," *Poult. Dis.*, vol. 70, No. SUP1, 1991, p. 73.

Rose et al., "Immunity to Coccidia in Chickens: Adoptive Transfer with Peripheral Blood Lymphocytes and Spleen Cells," *Parasite Immunology*, vol. 54, No. 3, May, 1982, p. 171–175.

Rose et al., "Coccidiosis: Rapid Depletion of Circulatory lymphocytes After Challenge of Immune Chickens with Parasite Antigens," *Infection and Immunity*, vol. 45, No. 1, Jul. 1984.

*Primary Examiner*—Laurie Scheiner
*Attorney, Agent, or Firm*—Mary E. Gormley

[57] ABSTRACT

This invention relates to novel Eimeria proteins with immunogenic properties as well as to DNA sequences encoding these proteins. These proteins can be administered to poultry thereby protecting the birds against coccidiosis. In addition the DNA encoding these proteins can be used for the preparation of a vector vaccine against coccidiosis.

17 Claims, 3 Drawing Sheets

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 1400 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v ) FRAGMENT TYPE: C-terminal ( v i ) ORIGINAL SOURCE:
( A ) ORGANISM: Eimeria maxima
( B ) STRAIN: Houghton
( D ) DEVELOPMENTAL STAGE: sporozoite ( v i i ) IMMEDIATE SOURCE:
( A ) LIBRARY: sporozoite cDNA cloned in Lambda ZAPII
( B ) CLONE: Em70-1

( i x ) FEATURE:
( A ) NAME/KEY: CDS
( B ) LOCATION: 1..1368

( x i ) SEQUENCE DESCRIPTION: SEQ ID NO:1:

```
GAA TTC GTG GAA GTT TTG GGT GAG GTC ATC TTA TGC AAG GAC AAG ATA    48
Glu Phe Val Glu Val Leu Gly Glu Val Ile Leu Cys Lys Asp Lys Ile
  1               5                  10                  15

ACA GCA CAG GAA TAT GCA GTA AAA GTA ATA TCT AAA CGT CAA GTA AAA    96
Thr Ala Gln Glu Tyr Ala Val Lys Val Ile Ser Lys Arg Gln Val Lys
             20                  25                  30

CAG AAG ACA GAT AAA GAA TTA TTA TTA AAA GAA GTT GAA TTA TTA AAG   144
Gln Lys Thr Asp Lys Glu Leu Leu Leu Lys Glu Val Glu Leu Leu Lys
         35                  40                  45

AAA TTA GAT CAT CCT AAT ATC ATG AAA TTA TAT GAA TTC TTT GAG GAT   192
Lys Leu Asp His Pro Asn Ile Met Lys Leu Tyr Glu Phe Phe Glu Asp
     50                  55                  60

AAA GGA TAC TTT TAT CTT GTT ACA GAA GTA TAT ACA GGA GGA GAA TTA   240
Lys Gly Tyr Phe Tyr Leu Val Thr Glu Val Tyr Thr Gly Gly Glu Leu
 65                  70                  75                  80

TTT GAT GAA ATT ATT AAT CGA AAA AGA TTC AGC GAG GCG GAT GCA GCT   288
Phe Asp Glu Ile Ile Asn Arg Lys Arg Phe Ser Glu Ala Asp Ala Ala
                 85                  90                  95
```

| | | | | | | | | | | | | | | | | |
|---|---|---|---|---|---|---|---|---|---|---|---|---|---|---|---|---|
| CGT | ATA | GTA | CGT | CAG | GTT | CTA | TCG | GGT | ATA | AAT | TAT | ATG | CAT | CGT | AAT | 336 |
| Arg | Ile | Val | Arg | Gln | Val | Leu | Ser | Gly | Ile | Asn | Tyr | Met | His | Arg | Asn | |
| | | | 100 | | | | 105 | | | | | 110 | | | | |
| AAA | ATA | GTT | CAT | AGA | GAT | TTA | AAG | CCA | GAG | AAT | TTA | TTA | TTA | GAG | AAT | 384 |
| Lys | Ile | Val | His | Arg | Asp | Leu | Lys | Pro | Glu | Asn | Leu | Leu | Leu | Glu | Asn | |
| | | | 115 | | | | 120 | | | | | 125 | | | | |
| AAA | AAA | AAA | GAT | GCA | AAT | ATA | CGA | ATT | ATT | GAT | TTT | GGG | TTA | TCT | ACA | 432 |
| Lys | Lys | Lys | Asp | Ala | Asn | Ile | Arg | Ile | Ile | Asp | Phe | Gly | Leu | Ser | Thr | |
| | 130 | | | | | 135 | | | | | 140 | | | | | |
| CAT | TTT | GAG | CCC | CAA | AAA | AAA | ATG | AAG | GAT | AAA | ATC | GGG | ACC | GCG | TAC | 480 |
| His | Phe | Glu | Pro | Gln | Lys | Lys | Met | Lys | Asp | Lys | Ile | Gly | Thr | Ala | Tyr | |
| 145 | | | | | 150 | | | | | 155 | | | | | 160 | |
| TAC | ATT | GCC | CCT | GAG | GTG | CTG | CAC | GGA | ACA | TAC | GAT | GAG | AAA | TGC | GAC | 528 |
| Tyr | Ile | Ala | Pro | Glu | Val | Leu | His | Gly | Thr | Tyr | Asp | Glu | Lys | Cys | Asp | |
| | | | | 165 | | | | 170 | | | | | 175 | | | |
| GTC | TGG | TCT | ACG | GGT | GTT | ATC | CTC | TAT | ATC | CTT | CTC | TCT | GGT | TGT | CCT | 576 |
| Val | Trp | Ser | Thr | Gly | Val | Ile | Leu | Tyr | Ile | Leu | Leu | Ser | Gly | Cys | Pro | |
| | | | 180 | | | | | 185 | | | | | 190 | | | |
| CCA | TTT | AAC | GGA | GCA | AAT | GAA | TTT | GAA | ATT | CTA | AAG | AAA | GTC | GAG | AAA | 624 |
| Pro | Phe | Asn | Gly | Ala | Asn | Glu | Phe | Glu | Ile | Leu | Lys | Lys | Val | Glu | Lys | |
| | | 195 | | | | | 200 | | | | | 205 | | | | |
| GGA | AAA | TTC | ACC | TTC | GAT | TTA | CCA | CAG | TGG | CGT | AAG | GTT | AGC | GAG | CCA | 672 |
| Gly | Lys | Phe | Thr | Phe | Asp | Leu | Pro | Gln | Trp | Arg | Lys | Val | Ser | Glu | Pro | |
| | 210 | | | | | 215 | | | | | 220 | | | | | |
| GCA | AAA | GAT | TTA | ATT | AGG | AAG | ATG | TTA | GCA | TAT | GTA | CCC | TCA | ATG | CGT | 720 |
| Ala | Lys | Asp | Leu | Ile | Arg | Lys | Met | Leu | Ala | Tyr | Val | Pro | Ser | Met | Arg | |
| 225 | | | | | 230 | | | | | 235 | | | | | 240 | |
| ATA | TCA | GCA | AAA | GAT | GCA | TTA | GAT | CAT | CCA | TGG | ATA | AAA | AGT | ACA | GAT | 768 |
| Ile | Ser | Ala | Lys | Asp | Ala | Leu | Asp | His | Pro | Trp | Ile | Lys | Ser | Thr | Asp | |
| | | | | 245 | | | | | 250 | | | | | 255 | | |
| GTT | ACT | GCT | AAG | GAT | AGT | ATT | AAT | CTT | CCT | TCT | CTT | GAG | AGT | ACT | ATA | 816 |
| Val | Thr | Ala | Lys | Asp | Ser | Ile | Asn | Leu | Pro | Ser | Leu | Glu | Ser | Thr | Ile | |
| | | | 260 | | | | | 265 | | | | | 270 | | | |
| CTT | AAT | ATC | AGG | CAG | TTC | CAG | GGT | ACA | CAG | AAG | CTT | GCT | GCT | GCT | GCT | 864 |
| Leu | Asn | Ile | Arg | Gln | Phe | Gln | Gly | Thr | Gln | Lys | Leu | Ala | Ala | Ala | Ala | |
| | | 275 | | | | | 280 | | | | | 285 | | | | |
| CTG | CTG | TAC | ATG | GGG | AGT | AAA | TTA | ACA | ACA | AAT | GAG | GAG | ACA | GAC | GAA | 912 |
| Leu | Leu | Tyr | Met | Gly | Ser | Lys | Leu | Thr | Thr | Asn | Glu | Glu | Thr | Asp | Glu | |
| | 290 | | | | | 295 | | | | | 300 | | | | | |
| TTG | AAT | AAA | ATC | TTC | CAG | AAG | ATG | GAT | AAG | AAC | GGA | GAC | GGA | CAA | CTC | 960 |
| Leu | Asn | Lys | Ile | Phe | Gln | Lys | Met | Asp | Lys | Asn | Gly | Asp | Gly | Gln | Leu | |
| 305 | | | | | 310 | | | | | 315 | | | | | 320 | |
| GAT | AAA | CAA | GAA | TTA | ATG | GAG | GGT | TAT | GTT | GAA | TTA | ATG | AAG | CTA | AAA | 1008 |
| Asp | Lys | Gln | Glu | Leu | Met | Glu | Gly | Tyr | Val | Glu | Leu | Met | Lys | Leu | Lys | |
| | | | | 325 | | | | | 330 | | | | | 335 | | |
| GGA | GAA | GAT | GTT | TCT | GTA | TTA | GAC | AAG | AGT | GCA | ATT | GAG | ACA | GAA | GTT | 1056 |
| Gly | Glu | Asp | Val | Ser | Val | Leu | Asp | Lys | Ser | Ala | Ile | Glu | Thr | Glu | Val | |
| | | | 340 | | | | | 345 | | | | | 350 | | | |
| GAA | CAA | GTT | CTT | GAG | GCT | GTA | GAC | TTC | GAT | AAG | AAT | GGA | TTT | ATT | GAA | 1104 |
| Glu | Gln | Val | Leu | Glu | Ala | Val | Asp | Phe | Asp | Lys | Asn | Gly | Phe | Ile | Glu | |
| | | 355 | | | | | 360 | | | | | 365 | | | | |
| TAT | TCA | GAA | TTC | GTG | ACG | GTG | GCA | ATG | GAT | AGA | AGA | ACT | CTG | TTA | TCA | 1152 |
| Tyr | Ser | Glu | Phe | Val | Thr | Val | Ala | Met | Asp | Arg | Arg | Thr | Leu | Leu | Ser | |
| | 370 | | | | | 375 | | | | | 380 | | | | | |
| AGA | CAA | AGA | CTT | GAA | AGA | GCA | TTC | GAG | ATG | TTC | GAC | TCG | GAT | GGA | TCA | 1200 |
| Arg | Gln | Arg | Leu | Glu | Arg | Ala | Phe | Glu | Met | Phe | Asp | Ser | Asp | Gly | Ser | |
| 385 | | | | | 390 | | | | | 395 | | | | | 400 | |
| GGA | AAA | ATC | TCC | TCC | TCT | GAA | TTA | GCT | ACT | ATA | TTT | GGT | GTA | AGC | GAG | 1248 |
| Gly | Lys | Ile | Ser | Ser | Ser | Glu | Leu | Ala | Thr | Ile | Phe | Gly | Val | Ser | Glu | |
| | | | | 405 | | | | | 410 | | | | | 415 | | |

```
TTA  GAC  TCG  GAG  GCA  TGG  CGT  CGC  GTA  TTA  GCA  GAA  GTT  GAT  CGA  AAT       1296
Leu  Asp  Ser  Glu  Ala  Trp  Arg  Arg  Val  Leu  Ala  Glu  Val  Asp  Arg  Asn
              420                     425                     430

AAT  GAC  GGA  GAA  GTT  GAC  TTT  GAG  GAA  TTT  CAG  CAA  ATG  CTT  CTT  AAA       1344
Asn  Asp  Gly  Glu  Val  Asp  Phe  Glu  Glu  Phe  Gln  Gln  Met  Leu  Leu  Lys
              435                     440                     445

TTA  TGT  GGT  AAT  ACT  GCA  GCA  GAA  TAAATAAATA AATAAAAAAA AAAAAAAAA              1398
Leu  Cys  Gly  Asn  Thr  Ala  Ala  Glu
     450                     455

AA                                                                                    1400
```

( 2 ) INFORMATION FOR SEQ ID NO:2:

( i ) SEQUENCE CHARACTERISTICS:
        ( A ) LENGTH: 456 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Glu  Phe  Val  Glu  Val  Leu  Gly  Glu  Val  Ile  Leu  Cys  Lys  Asp  Lys  Ile
 1              5                    10                       15

Thr  Ala  Gln  Glu  Tyr  Ala  Val  Lys  Val  Ile  Ser  Lys  Arg  Gln  Val  Lys
              20                    25                       30

Gln  Lys  Thr  Asp  Lys  Glu  Leu  Leu  Leu  Lys  Val  Glu  Leu  Leu  Lys
              35                    40                       45

Lys  Leu  Asp  His  Pro  Asn  Ile  Met  Lys  Leu  Tyr  Glu  Phe  Phe  Glu  Asp
     50                    55                       60

Lys  Gly  Tyr  Phe  Tyr  Leu  Val  Thr  Glu  Val  Tyr  Thr  Gly  Gly  Glu  Leu
 65                   70                       75                           80

Phe  Asp  Glu  Ile  Ile  Asn  Arg  Lys  Arg  Phe  Ser  Glu  Ala  Asp  Ala  Ala
                    85                    90                       95

Arg  Ile  Val  Arg  Gln  Val  Leu  Ser  Gly  Ile  Asn  Tyr  Met  His  Arg  Asn
              100                   105                      110

Lys  Ile  Val  His  Arg  Asp  Leu  Lys  Pro  Glu  Asn  Leu  Leu  Leu  Glu  Asn
              115                   120                      125

Lys  Lys  Lys  Asp  Ala  Asn  Ile  Arg  Ile  Ile  Asp  Phe  Gly  Leu  Ser  Thr
     130                   135                      140

His  Phe  Glu  Pro  Gln  Lys  Lys  Met  Lys  Asp  Lys  Ile  Gly  Thr  Ala  Tyr
145                  150                      155                          160

Tyr  Ile  Ala  Pro  Glu  Val  Leu  His  Gly  Thr  Tyr  Asp  Glu  Lys  Cys  Asp
              165                   170                      175

Val  Trp  Ser  Thr  Gly  Val  Ile  Leu  Tyr  Ile  Leu  Leu  Ser  Gly  Cys  Pro
              180                   185                      190

Pro  Phe  Asn  Gly  Ala  Asn  Glu  Phe  Glu  Ile  Leu  Lys  Lys  Val  Glu  Lys
              195                   200                      205

Gly  Lys  Phe  Thr  Phe  Asp  Leu  Pro  Gln  Trp  Arg  Lys  Val  Ser  Glu  Pro
      210                   215                      220

Ala  Lys  Asp  Leu  Ile  Arg  Lys  Met  Leu  Ala  Tyr  Val  Pro  Ser  Met  Arg
225                  230                      235                          240

Ile  Ser  Ala  Lys  Asp  Ala  Leu  Asp  His  Pro  Trp  Ile  Lys  Ser  Thr  Asp
              245                   250                      255

Val  Thr  Ala  Lys  Asp  Ser  Ile  Asn  Leu  Pro  Ser  Leu  Glu  Ser  Thr  Ile
              260                   265                      270

Leu  Asn  Ile  Arg  Gln  Phe  Gln  Gly  Thr  Gln  Lys  Leu  Ala  Ala  Ala  Ala
              275                   280                      285
```

| Leu | Leu | Tyr | Met | Gly | Ser | Lys | Leu | Thr | Thr | Asn | Glu | Glu | Thr | Asp | Glu |
| | 290 | | | | | 295 | | | | | 300 | | | | |
| Leu | Asn | Lys | Ile | Phe | Gln | Lys | Met | Asp | Lys | Asn | Gly | Asp | Gly | Gln | Leu |
| 305 | | | | | 310 | | | | | 315 | | | | | 320 |
| Asp | Lys | Gln | Glu | Leu | Met | Glu | Gly | Tyr | Val | Glu | Leu | Met | Lys | Leu | Lys |
| | | | | 325 | | | | | 330 | | | | | 335 | |
| Gly | Glu | Asp | Val | Ser | Val | Leu | Asp | Lys | Ser | Ala | Ile | Glu | Thr | Glu | Val |
| | | | 340 | | | | | 345 | | | | | 350 | | |
| Glu | Gln | Val | Leu | Glu | Ala | Val | Asp | Phe | Asp | Lys | Asn | Gly | Phe | Ile | Glu |
| | | 355 | | | | | 360 | | | | | 365 | | | |
| Tyr | Ser | Glu | Phe | Val | Thr | Val | Ala | Met | Asp | Arg | Arg | Thr | Leu | Leu | Ser |
| | 370 | | | | | 375 | | | | | 380 | | | | |
| Arg | Gln | Arg | Leu | Glu | Arg | Ala | Phe | Glu | Met | Phe | Asp | Ser | Asp | Gly | Ser |
| 385 | | | | | 390 | | | | | 395 | | | | | 400 |
| Gly | Lys | Ile | Ser | Ser | Ser | Glu | Leu | Ala | Thr | Ile | Phe | Gly | Val | Ser | Glu |
| | | | | 405 | | | | | 410 | | | | | 415 | |
| Leu | Asp | Ser | Glu | Ala | Trp | Arg | Arg | Val | Leu | Ala | Glu | Val | Asp | Arg | Asn |
| | | | 420 | | | | | 425 | | | | | 430 | | |
| Asn | Asp | Gly | Glu | Val | Asp | Phe | Glu | Glu | Phe | Gln | Gln | Met | Leu | Leu | Lys |
| | | 435 | | | | | 440 | | | | | 445 | | | |
| Leu | Cys | Gly | Asn | Thr | Ala | Ala | Glu | | | | | | | | |
| | 450 | | | | | 455 | | | | | | | | | |

(2) INFORMATION FOR SEQ ID NO: 3:

(i) SEQUENCE CHARACTERISTICS:
      (A) LENGTH: 242 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iii) ANTI-SENSE: NO (v) FRAGMENT TYPE: C-terminal (vi) ORIGINAL SOURCE:
      (A) ORGANISM: Eimeria maxima
      (B) STRAIN: Houghton
      (D) DEVELOPMENTAL STAGE: Sporozoite (vii) IMMEDIATE SOURCE:
      (A) LIBRARY: sporozoite cDNA cloned in Lambda ZAPII
      (B) CLONE: Em70-4, 5'end of clone (ix) FEATURE:
      (A) NAME/KEY: CDS
      (B) LOCATION: 3..242

(xi) SEQUENCE DESCRIPTION: SEQ ID NO: 3:

| GT | GCT | ATT | GCA | GGT | CTT | AAT | GTT | ATT | CGT | ATT | ATT | AAT | GAA | CCT | ACT | 47 |
| | Ala | Ile | Ala | Gly | Leu | Asn | Val | Ile | Arg | Ile | Ile | Asn | Glu | Pro | Thr | |
| | | 1 | | | 5 | | | | | 10 | | | | | 15 | |
| GCT | GCT | GCT | ATT | GCT | TAC | GGT | CTT | GAT | AAA | AAA | GAC | GAA | AAG | ACT | ATC | 95 |
| Ala | Ala | Ala | Ile | Ala | Tyr | Gly | Leu | Asp | Lys | Lys | Asp | Glu | Lys | Thr | Ile | |
| | | | | 20 | | | | | 25 | | | | | 30 | | |
| CTT | GTC | TAC | GAT | CTT | GGT | GGT | GGT | ACC | TTT | GAT | GTA | TCC | GTC | CTT | GTT | 143 |
| Leu | Val | Tyr | Asp | Leu | Gly | Gly | Gly | Thr | Phe | Asp | Val | Ser | Val | Leu | Val | |
| | | | 35 | | | | | 40 | | | | | 45 | | | |
| ATT | GAC | AAC | GGT | GTA | TTC | GAA | GTC | CAT | GCA | ACT | TCA | GGT | GAT | ACA | CAT | 191 |
| Ile | Asp | Asn | Gly | Val | Phe | Glu | Val | His | Ala | Thr | Ser | Gly | Asp | Thr | His | |
| | | | 50 | | | | | 55 | | | | | 60 | | | |

```
     CTA  GGA  GGA  GAA  GAT  TTC  GAT  CAG  AGA  GTA  ATG  GAT  CAC  TTC  CTG  AAG       239
     Leu  Gly  Gly  Glu  Asp  Phe  Asp  Gln  Arg  Val  Met  Asp  His  Phe  Leu  Lys
          65                       70                      75

ATT                                                                                  242
     Ile
     80
```

( 2 ) INFORMATION FOR SEQ ID NO: 4:

( i ) SEQUENCE CHARACTERISTICS:
        ( A ) LENGTH: 80 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

```
     Ala  Ile  Ala  Gly  Leu  Asn  Val  Ile  Arg  Ile  Ile  Asn  Glu  Pro  Thr  Ala
     1              5                        10                      15

Ala  Ala  Ile  Ala  Tyr  Gly  Leu  Asp  Lys  Lys  Asp  Glu  Lys  Thr  Ile  Leu
                    20                  25                      30

Val  Tyr  Asp  Leu  Gly  Gly  Gly  Thr  Phe  Asp  Val  Ser  Val  Leu  Val  Ile
               35                  40                      45

Asp  Asn  Gly  Val  Phe  Glu  Val  His  Ala  Thr  Ser  Gly  Asp  Thr  His  Leu
          50                  55                      60

Gly  Gly  Glu  Asp  Phe  Asp  Gln  Arg  Val  Met  Asp  His  Phe  Leu  Lys  Ile
          65                  70                      75                           80
```

( 2 ) INFORMATION FOR SEQ ID NO: 5:

( i ) SEQUENCE CHARACTERISTICS:
        ( A ) LENGTH: 250 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i i i ) ANTI-SENSE: NO ( v i ) ORIGINAL SOURCE:
        ( A ) ORGANISM: Eimeria maxima
        ( B ) STRAIN: Houghton
        ( D ) DEVELOPMENTAL STAGE: Sporozoite ( v i i ) IMMEDIATE SOURCE:
        ( A ) LIBRARY: sporozoite cDNA cloned in Lambda ZAPII
        ( B ) CLONE: Em70-4, 3'end of clone ( x i ) SEQUENCE DESCRIPTION: SEQ ID NO: 5:

```
TTTTTTTTT   TTTTTTTCT   ATCCTCATCT   GCAAACTTTT   CTGCTTCTTG   TATCTACCTT       60

ACTATCTCAT  CAGGAGTAAG  TCTTCCTTAT   CATTAGTTAT   TGTTATTTTC   TCGCTCTTTC      120

CTGTTCCTTT  ATCTACAGCA  CTTACATTCA   ATATACCGTT   CCTGTCTACA   TCAAATGTTA      180

CATCTATCTG  TGGTACACCA  CGAGGTGCAG   GAGGTATTCC   TGTTAATTCA   AACTTTCCTA      240

ATAAATGGTT                                                                    250
```

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:6:

CACGAATTCA CTATCGATTC TGGAACCTTC AGAGG 35

( 2 ) INFORMATION FOR SEQ ID NO:7:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CTGGTTCGGC CCACCTCTGA AGGTTCCAGA ATCGATAG 38

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:8:

TATACCCGAT AGAACCTGAC G 21

( 2 ) INFORMATION FOR SEQ ID NO:9:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:9:

GATCTAAATA TGCCGGATTA TTCATACCGT CCCACCATCG GTACCG 46

( 2 ) INFORMATION FOR SEQ ID NO:10:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GATCCGGTAC CGATGGTGGG ACGGTATGAA TAATCCGGCA TATTTA 46

COCCIDIOSIS POULTRY VACCINE

This is a continuation, of application Ser. No. 08/338,057 filed Nov. 10, 1994.

FIELD OF THE INVENTION

The present invention relates to a protein derived from an Eimeria species, in particular Eimeria maxima, which is capable of stimulating immune lymphocytes. It also relates to a nucleic acid sequence encoding all or an antigenically significant part of this protein, a recombinant vector comprising such a nucleic acid sequence, a host cell or organism transformed with such a recombinant vector and a vaccine for the protection of poultry against coccidiosis.

BACKGROUND OF THE INVENTION

Coccidiosis is a disease caused by infection with one or more of the many species of coccidia, intracellular protozoal parasites of the subphylum Apicomplexa and the genus Eimeria. Poultry is defined herein as domesticated birds that serve as a source of eggs or meat and that include such commercially important kinds as chickens, turkeys, ducks, geese, guinea fowl, pheasants, pigeons and peafowl.

Coccidiosis in chickens is known to be caused by several different species of Eimeria, namely *Eimeria acervulina, E. maxima, E. tenella, E. necatrix, E. brunetti, E. mitis, E. praecox, E. mivati* and *E. hagani*. Some people, however, doubt the true existence of the last two species. Low level infection with any of these Eimeria species results in a protective immunity to reinfection.

The species do differ in their pathogenic effect on chickens, the type of chicken also playing a role; thus, a broiler chicken will be subjected to a great deal of damage by a parasite such as *E. acervulina* or *E. maxima* because these parasitise large portions of the small intestine, where food digestion plays a major role.

*E. maxima* is the most immunogenic of the species listed above, producing good natural protection following infection. There are, however, strain variations with little or no cross protection between strains.

During the life cycle, the Eimeria parasite passes through a number of stages. The life cycle begins when the chicken ingests the infectious stage, known as the sporulating oocyst, during ground feeding or by inhalation of dust. In the case of *E. maxima*, the oocyst is unusually large. The wall of the sporulated oocyst is ruptured by a combination of mechanical grinding action and chemical action in the gizzard and intestinal tract, resulting in the release of four sporocysts. The sporocysts pass into the duodenum where they are exposed to bile and digestive enzymes resulting in the release of an average of ten sporozoites per sporocyst.

The sporozoites are mobile and search for suitable host epithelium cells in order to penetrate and reproduce in them. Following infection of an epithelium cell, the parasite enters the schizont phase of its life cycle, producing from 8 to 16 to >200 merozoites per schizont. Once released from the schizont, the merozoites are free to infect further epithelium cells. After from two to five of these asexual reproduction cycles, the intracellular merozoites grow into sexual forms known as the female or macrogametocyte and the male or microgametocyte. Following fertilization of the macrogametocyte by the microgametes released from the microgametocyte, a zygote is formed which creates a cyst wall about itself. The newly formed oocyst is passed out of the infected chicken with the droppings.

With the correct environmental conditions of temperature and humidity and sufficient oxygen in the air, the oocyst will sporulate into the infectious stage, ready to infect a new host and thereby spreading the disease. Thus no intermediate host is required for transfer of the parasite from bird to bird.

The result of the Eimeria parasite infecting the digestive tract of a chicken may be a reduction in weight gain, decreased feed conversion, cessation of egg production and, in many cases, death. The increase in intensive production of poultry has been accompanied by severe losses due to this parasite; indeed, coccidiosis has become the most economically important parasitic disease. In the Netherlands, the losses that poultry farmers suffer every year run into millions of guilders; in 1986 the loss was about 13 million guilders. In the same year, a loss of 300 million dollars was suffered in the United States.

In the past, several methods have been used in attempts to control coccidiosis. Prior to the advent of chemotherapeutic agents, improved sanitation using disinfectants, together with the mechanical removal of litter, was the main method employed; sufficient oocysts, however, usually remained to transmit the disease.

The introduction of coccidiostatic agents in the feed or drinking water, in addition to good management, resulted in some success at disease control. Such agents have been found to suffer from a drop in effectiveness over the years, due partly to the development of drug resistant strains of coccidia. Furthermore, several chemotherapeutic agents have been found to leave residues in the meat, making it unsuitable for consumption.

Attempts have been made to control the disease immunologically by administering to chickens a live vaccine comprising oocysts from all seven species of Eimeria, the oocysts administered being from precocious lines. Such precocious lines are obtained by inoculating chickens with a wild population of an Eimeria species and collecting the very first parasites that are excreted as a result of the infection. The collected parasites are put back into chickens and the cycle is repeated several times. Eventually a precocious line of parasite is produced which has fewer cycles of asexual reproduction in the gut. Thus such lines retain their immunogenicity, whilst producing fewer parasites in the gut with less consequential damage being caused to the host chicken. The disadvantage of this type of vaccine is that it is expensive to produce because of the necessity of producing it in live chickens and its lower reproductive potential.

The advent of genetic engineering has provided new methods for producing effective vaccines. Using these methods, the DNA coding for the antigenic proteins of some pathogenic microorganisms has been cloned into such host microorganisms as *Escherichia coli*, with the result that the protein has been expressed at sufficiently high levels such that it can be incorporated into a vaccine. The advantage of proteins produced in this way is that they are noninfectious and are relatively cheap to produce. In this way, vaccines have been prepared against a number of viruses such as hepatitis, herpes simplex and foot and mouth disease.

Attempts have been made to genetically engineer a coccidiosis vaccine. European patent application No. 337 589 describes the isolation of a Group B *Eimeria tenella* protein and its insertion into a novel expression vector which, in turn, has been used to transform appropriate hosts. Patent Cooperation Treaty Application WO 92/04461 describes the construction of a microorganism that produces an antigenic protein using either the "mRNA route" or the "nuclear DNA route". In this way, certain antigens from *E. tenella* and *E.* maxima were prepared and sequenced. Taking this type of route to prepare antigens for incorporation into a vaccine relies only upon selecting antigens which could induce antibodies in an heterologous species. This approach does not necessarily end up with selecting the most protective antigen.

From H. S. Lillehoj (Vet. Immunol. Immunopath., 13, 321–330, 1986) it can be conceived that development of protective immunity in chickens infected with coccidia may be due to the development of a species-specific T cell response.

SUMMARY OF THE INVENTION

It has now been found that by fractionating Eimeria parasites and selecting proteins that stimulate immune T-lymphocytes, then preparing vectors containing the nucleic acid coding for such proteins and subsequently preparing a vaccine containing such proteins, a more effectively protective coccidiosis vaccine may be produced.

According to one aspect of the present invention, there is provided a purified *Eimeria maxima* T-lymphocyte stimulatory protein or an immunogenically active part thereof. Such a protein is essentially free from the whole parasite or other proteins with which they are ordinarily associated.

According to a second aspect of the invention, there is provided a nucleic acid sequence encoding all or a substantial part, in particular the immunologically active part, of a purified *Eimeria maxima* T-lymphocyte stimulatory protein. Such a nucleic acid sequence may be operatively linked to expression control sequences resulting in a recombinant nucleic acid molecule which, when inserted into a suitable vector, results in a recombinant vector capable of expressing the nucleic acid sequence.

Such a recombinant vector, or nucleic acid sequence as defined above, may be used to transform a suitable host cell or organism. Such a transformed host cell or organism may, in turn, be used to produce the stimulatory protein for incorporation into a vaccine for the protection of poultry against coccidiosis. Alternatively, the transformed host cell or organism may itself be incorporated into a vaccine.

In general, the term "protein" refers to a molecular chain of amino acids with biological activity. A protein is not of a specific length and can, if required, be modified in vivo or in vitro, by, for example, glycosylation, amidation, carboxylation or phosphorylation; thus, inter alia, peptides, oligopeptides and polypeptides are included within the definition.

More particularly, this invention provides T-lymphocyte stimulatory proteins, or immunogenically active parts thereof, which have the amino acid sequence shown in SEQ ID NO. 2 and 4 and their biologically functional equivalents or variants.

The biologically functional equivalents or variants of the proteins specifically disclosed herein are proteins derived from the abovenoted amino acid sequences, for example by deletions, insertions and/or substitutions of one or more amino acids, but retain one or more immunogenic determinants of the Eimeria antigens, i.e. said variants have one or more epitopes capable of eliciting an immune response in a host animal.

It will be understood that, for the particular proteins embraced herein, natural variations can exist between individual Eimeria parasites or strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435–1441, 1985) and determining the functional similarity between homologous proteins. Such amino acid substitutions of the exemplary embodiments of this invention are within the scope of the invention as long as the resulting proteins retain their immunoreactivity.

The invention further provides isolated and purified nucleic acid sequences encoding the above mentioned proteins of Eimeria. Such nucleic acid sequences are shown in SEQ. ID. NOS. 1,3 and 5. It is well known in the art that the degeneracy of the genetic code permits substitution of bases in the codon resulting in another codon but still coding for the same amino acid, e.g. the codon for the amino acid glutamic acid is both GAT and GAA. Consequently, it is clear that, for the expression of a protein with the amino acid sequence shown in SEQ. ID. NOS. 2 and 4, the nucleic acid sequence may have a codon composition different from the nucleic acid sequence shown in SEQ. ID. NOS. 1 and 3, respectively.

DETAILED DESCRIPTION OF THE INVENTION

Figures 1, 2:
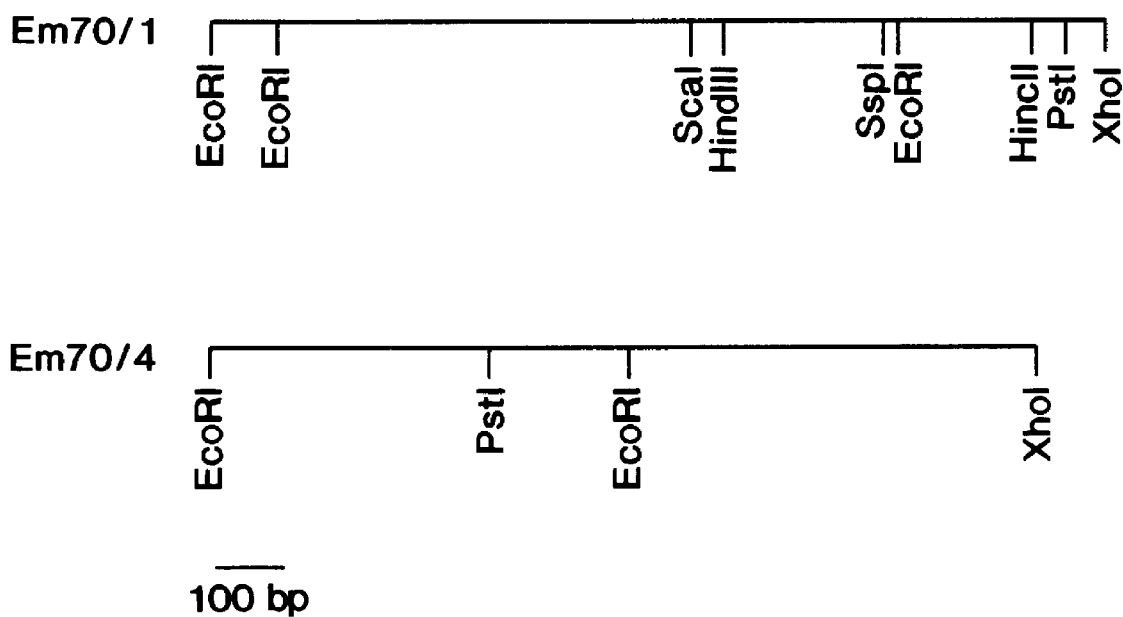
FIG. 1 shows a Western blot of *E. maxima* sporozoites screened with anti-70kD sera.
FIG. 2 shows the restriction maps of p70 cDNA inserts (5'-3').

*Eimeria maxima* parasites were produced by passage through chickens as described by Long et al (Folio Vet. Lat., 1976, 6, 201–207). Oocysts were isolated from the faeces of the infected chickens, sporulated and then purified by floatation in saturated sodium chloride. The sporulated oocysts were then used to infect pathogen-free 4 week old chickens. A further dose of sporulated oocysts was administered to the birds in order to boost their immune response.

A preparation of sporulated oocysts purified by floatation as described above was subjected to vibration in a disintegrator in order to release sporozoites. The sporozoites were treated with proteolytic enzymes in order to release sporozoites which were then washed and purified by ion-exchange chromatography according to the method of Schmatz et al (J. Protozool., 1984, 31, 181–183). The sporozoites were suspended in buffer, boiled in a water bath and spun prior to loading on a polyacrylamide gel for SDS-PAGE(sodium dodecyl sulphate polyacrylamide gel electrophoresis).

Molecular mass markers were run on the same gel in order to extrapolate the molecular mass of the Eimeria antigens. The gel was electrophoresed onto nitrocellulose paper by the method of Towbin and Gordon, (J. Immunol. Methods., 1984, 72, 313–340). The nitrocellulose paper was then washed and visualised by Aurodye staining according to the manufacturer's instructions.

Protein bands were excised from the nitrocellulose paper, cut into small pieces and transferred to glass vials. The nitrocellulose pieces were then solubilised in dimethyl sulphoxide (DMSO) and left for a period of time to ensure solubilization, after which the nitrocellulose particles were precipitated by dropwise addition of carbonate/bicarbonate buffer with vigorous vortexing. Samples were then centrifuged, the pellets of nitrocellulose particles were washed several times after which they were resuspended and divided into small aliquots.

In order to determine whether any of the protein bands from the electrophoresis gel stimulated the lymphocytes from infected birds, blood was withdrawn by venopuncture from the chickens infected as described above, for use in a lymphocyte proliferation assay. The blood was centrifuged at 600 g, after 10 minutes the suspension of cells above the sedimented erythrocytes was removed and centrifuged at 400 g for a further 10 minutes. The cells deposited after the second centrifugation were washed several times and finally resuspended. The resuspended cells were cultured in round bottomed plates together with the diluted resuspended nitrocellulose particles. Control wells were set up containing nitrocellulose particles devoid of protein.

The lymphocyte cultures were incubated for 96 hours, during the last 16 hours of which the cultures were pulsed with 3H-thymidine, following which the cells were harvested onto glass microfibre filters. After drying, the filters were placed in scintillation vials to which was added liquid scintillation cocktail (Scintillator 299 [registered trade mark] Packard, Caversham, U.K.) and the radioactivity was measured in a scintillation spectrophotometer. The results were expressed as a stimulation index (SI) obtained using the following formula:

$$SI = cpm1/cpm2$$

where:
cpm1=average counts per minute of triplicate cultures incubated with NC particles bearing protein.
cpm2=average counts per minute of triplicate cultures incubated with NC particles devoid of protein.

By this method mostly T-lymphocytes are proliferating.

The results showed that although the stimulation index varied for different birds and different gels, a protein band, with a relative molecular mass (Mr) of approximately 70.000 D, gave consistant stimulation of lymphocytes from immunised but not control birds.

Following this discovery, a fresh preparation of E. maxima sporozoites was separated by SDS-PAGE and transferred to nitrocellulose as described above. A protein band with a Mr of 70.000 D (p70) was excised, solubilised as described, washed in phosphate buffered saline (PBS) and then resuspended in PBS. This suspension was inoculated subcutaneously into rabbits, the injections being repeated every 2 weeks. Two weeks after each injection the rabbits were bled by venapuncture of a lateral ear vein. Rabbit anti-p70 serum was obtained after 5 boosts as determined by Western blotting.

Total ribonucleic acid (RNA) was extracted and purified from E. maxima sporozoites by centrifugation through a gradient of cesium trifluoroacetate. In order to separate the messenger RNA (mRNA) from non-mRNA, columns of oligo dT CELLULOSE (poly[A] Quik, Stratagene) were used according to the manufacturer's instructions. The poly (A)+ RNA or mRNA was then eluted from the column overnight using sodium acetate in absolute ethanol.

Copy deoxyribonucleic acid (cDNA) was synthesised from the mRNA using a ZAP-cDNA (registered trade mark) synthesis kit (Stratagene). The first strand of cDNA was synthesised using an oligo dT template (containing an XhoI restriction site) and Moloney-Murine Leukaemia Virus reverse transcriptase. The cytosine residues in the first strand of cDNA were methylated in order to protect the cDNA from digestion by restriction enzymes to be used later in the cloning protocol. The second strand of cDNA was synthesised using RNAse H and DNA polymerase I followed by end-repairing using T4 DNA polymerase. EcoRI adapters were ligated to the blunt ended cDNA by T4 DNA ligase. Digestion with XhoI produced cDNA with an XhoI compatible 3' end and an EcoRI compatible 5' end.

The cDNA was ligated to EcoRI/XhoI digested and dephosphorylated Uni-ZAP XR vector using T4 DNA ligase. The resulting primary libraries (Emx 8 and Emx 9) were plated and amplified on E. coli SURE cell. It was found that the Emx8 library gave 65% recombinants, whereas the Emx9 library gave 55% recombinants.

The two libraries, Emx8 and Emx9, were screened using rabbit anti-p70 serum, prepared as described above. Positive plaques were picked out, and rescreened until the positives were plaque pure.

The cDNA from clones in the two libraries, Emx8 and Emx9 were subcloned into plasmid pUC19 and analysed by digestion with restriction endonucleases. Alternatively, the cDNAs were subjected to plasmid rescue from lambda Zap using in vivo excision and subsequently analysed by digestion with restriction endonucleases.

In this way several different clones were identified. Selected antisera for two of the clones crossreacted with different spots recognised by the anti-p70 antisera on blots of E. maxima sporozoites separated by 2d PAGE, these clones were then selected for DNA sequence analysis. This was carried out by random subcloning and sequencing using the M13/dideoxynucleotide chain termination method described by Bankier et al. (Techniques in the Life Sciences (Biochemistry) 85: techniques in Nucleic Acids Biochemstry 1–34, 1983).

A nucleic acid sequence according to the present invention may be isolated from an Eimeria maxima strain and multiplied by recombinant DNA techniques including polymerase chain reaction (PCR) technology or may be chemically synthesized in vitro by techniques known in the art.

A nucleic acid sequence according to the invention can be ligated to various replication effecting DNA sequences with which it is not associated, or linked in nature, resulting in a so-called recombinant vector which can be used for the transformation of a suitable host. Useful recombinant vectors are preferably derived from plasmids, bacteriophages, cosmids or viruses.

Specific vectors or cloning vehicles which can be used to clone nucleic acid sequences according to the invention are known in the art and include inter alia plasmid vectors such as pBR322, the various pUC, PGEM and Bluescript plasmids; bacteriophages, e.g. lambdagt-Wes, Charon 28 and the M13 derived phages or viral vectors such as SV40, adenovirus or polyoma virus (see also Rodriguez, R. L. and D. T. Denhardt, ed., Vectors: A survey of molecular cloning vectors and their uses, Butterworths, 1988; Lenstra, J. A. et al., Arch. Virol., 110, 1–24, 1990). The methods to be used for the construction of a recombinant vector according to the invention are known to those of ordinary skill in the art and are inter alia set forth in Maniatis, T. et al. (Molecular Cloning A Laboratory Manual, second edition; Cold Spring Harbor Laboratory, 1989).

For example, the insertion of the nucleic acid sequence according to the invention into a cloning vector can easily be achieved when both the genes and the desired cloning vehicle have been cut with the same restriction enzyme(s) as complementary DNA termini are thereby produced.

Alternatively, it may be necessary to modify the restriction sites that are produced into blunt ends either by digesting the single-stranded DNA or by filling in the single-stranded termini with an appropriate DNA polymerase. Subsequently, blunt end ligation with an enzyme such as T4 DNA ligase may be carried out.

If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

"Transformation", as used herein, refers to the introduction of an heterologous nucleic acid sequence into a host cell, irrespective of the method used, for example direct uptake or transduction. The heterologous nucleic acid sequence may be maintained through autonomous replication or, alternatively, may be integrated into the host genome. If desired, the recombinant vectors are provided with appropriate control sequences compatible with the designated host. These sequences can regulate the expression of the inserted nucleic acid sequence. In addition to microorganisms, cell cultures derived from multicellular organisms may also be used as hosts.

The recombinant vectors according to the invention preferably contain one or more marker activities that may be used to select for desired transformants, such as ampicillin and tetracycline resistance in pBR322, ampicillin resistance and _peptide of β-galactosidase in pUC8.

A suitable host cell is a microorganism or cell which can be transformed by a nucleic acid sequence encoding a polypeptide or by a recombinant vector comprising such a nucleic acid sequence, and which can, if desired, be used to express said polypeptide encoded by said nucleic acid sequence. The host cell can be of prokaryotic origin, e.g. bacteria such as *Escherichia coli, Bacillus subtilis* and *Pseudomonas species*; or of eukaryotic origin such as yeasts, e.g. *Saccharomyces cerevisiae* or higher eukaryotic cells such as insect, plant or mammalian cells, including HeLa cells and Chinese hamster ovary (CHO) cells. Insect cells include the Sf9 cell line of *Spodoptera frugiperda* (Luckow et al., Biotechnology 6, 47–55, 1988). Information with respect to the cloning and expression of the nucleic acid sequence of the present invention in eukaryotic cloning systems can be found in Esser, K. et al. (Plasmids of Eukaryotes, Springer-Verlag, 1986).

In general, prokaryotes are preferred for the construction of the recombinant vectors useful in the present invention. *E. coli* K12 strains are particularly useful, especially DH5a or MC1061 strains.

For expression, nucleic acid sequences of the present invention are introduced into an expression vector, i.e. said sequences are operably linked to expression control sequences. Such control sequences may comprise promotors, enhancers, operators, inducers, ribosome binding sites etc. Therefore, the present invention provides a recombinant vector comprising a nucleic acid sequence encoding an Eimeria protein identified above operably linked to expression control sequences, which is capable of expressing the DNA sequences contained therein in (a) transformed host cell(s).

It should be understood, of course, that the nucleotide sequences inserted at the selected site of the cloning vector may include nucleotides which are not part of the actual structural gene for the desired polypeptide, or may include only a fragment of the complete structural gene for the desired protein as long as the transformed host will produce a polypeptide having at least one or more immunogenic determinants of an Eimeria protein antigen.

When the host cells are bacteria, useful expression control sequences which may be used include the Trp promotor and operator (Goeddel, et al., Nucl. Acids Res., 8, 4057, 1980); the lac promotor and operator (Chang, et al., Nature, 275, 615, 1978); the outer membrane protein promotor (Nakamura, K. and Inouge, M., EMBO J., 1, 771–775, 1982); the bacteriophage lambda promotors and operators (Remaut, E. et al., Nucl. Acids Res., 11, 4677–4688, 1983); the _amylase (*B. subtilis*) promotor and operator, termination sequences and other expression enhancement and control sequences compatible with the selected host cell. When the host cell is yeast, illustrative useful expression control sequences include, e.g., _mating factor. For insect cells the polyhedrin or p10 promoters of baculoviruses can be used (Smith, G. E. et al., Mol. Cell. Biol. 3, 2156–65, 1983). When the host cell is of mammalian origin illustrative useful expression control sequences include the SV-40 promotor (Berman, P. W. et al., Science, 222, 524–527, 1983) or the metallothionein promotor (Brinster, R. L., Nature, 296, 39–42, 1982) or a heat shock promotor (Voellmy et al., Proc. Natl. Acad. Sci. USA, 82, 4949–53, 1985). Alternatively, expression control sequences present in Eimeria may also be applied. For maximizing gene expression, see also Roberts and Lauer (Methods in Enzymology, 68, 473, 1979).

Therefore, the invention also comprises (a) host cell(s) containing a nucleic acid sequence or a recombinant nucleic acid molecule or a recombinant vector described above, capable of producing the Eimeria protein by expression of the nucleic acid sequence.

Immunization of poultry against Eimeria infection can be achieved by administering to the birds a protein according to the invention in an immunologically relevant context as a so-called subunit vaccine. The subunit vaccine according to the invention may comprise a protein in a pure form, optionally in the presence of a pharmaceutically acceptable carrier. The protein can optionally be covalently bonded to a non-related protein, which can be of advantage in the purification of the fusion product. Examples are β-galactosidase, protein A, prochymosine, blood clotting factor Xa, etc.

In some cases the ability to raise protective immunity using these proteins per se may be low. Small fragments are preferably conjugated to carrier molecules in order to raise their immunogenicity. Suitable carriers for this purpose are macromolecules, such as natural polymers (proteins like key hole limpet hemocyanin, albumin, toxins), synthetic polymers like polyamino acids (polylysine, polyalanine), or micelles of amphiphilic compounds like saponins. Alternatively these fragments may be provided as polymers thereof, preferably linear polymers.

If required, the proteins according to the invention which are to be used in a vaccine can be modified in vitro or in vivo, for example by glycosylation, amidation, carboxylation or phosphorylation.

An alternative to subunit vaccines is live vaccines. A nucleic acid sequence according to the invention is introduced by recombinant DNA techniques into a microorganism (e.g. a bacterium or virus) in such a way that the recombinant microorganism is still able to replicate, thereby expressing a polypeptide coded by the inserted nucleic acid sequence and eliciting an immune response in the infected host bird.

A preferred embodiment of the present invention is a recombinant vector virus comprising an heterologous nucleic acid sequence described above, capable of expressing the DNA sequence in (a) host cell(s) or host bird infected with the recombinant vector virus. The term "heterologous" indicates that the nucleic acid sequence according to the invention is not normally present in nature in the vector virus.

Furthermore, the invention also comprises (a) host cell(s) or cell culture infected with the recombinant vector virus, capable of producing the Eimeria protein by expression of the nucleic acid sequence.

For example the well known technique of in vivo homologous recombination can be used to introduce an heterologous nucleic acid sequence according to the invention into the genome of the vector virus.

First, a DNA fragment corresponding with an insertion region of the vector genome, i.e. a region which can be used for the incorporation of an heterologous sequence without disrupting essential functions of the vector such as those necessary for infection or replication, is inserted into a cloning vector according to standard recDNA techniques. Insertion-regions have been reported for a large number of microorganisms (e.g. EP 80,806, EP 110,385, EP 83,286, EP 314,569, WO 88/02022, WO 88/07088, U.S. Pat. No. 4,769,330 and U.S. Pat. No. 4,722,848).

Second, if desired, a deletion can be introduced into the insertion region present in the recombinant vector molecule obtained from the first step. This can be achieved for example by appropriate exonuclease III digestion or restriction enzyme treatment of the recombinant vector molecule from the first step.

Third, the heterologous nucleic acid sequence is inserted into the insertion-region present in the recombinant vector of the first step or in place of the DNA deleted from said recombinant vector. The insertion region DNA sequence should be of appropriate length as to allow homologous recombination with the vector genome to occur. Thereafter, suitable cells can be infected with wild-type vector virus or transformed with vector genomic DNA in the presence of the recombinant vector containing the insertion flanked by appropriate vector DNA sequences whereby recombination occurs between the corresponding regions in the recombinant vector and the vector genome. Recombinant vector progeny can now be produced in cell culture and can be selected for example genotypically or phenotypically, e.g. by hybridization, detecting enzyme activity encoded by a gene co-integrated along with the heterologous nucleic acid sequence, or detecting the antigenic heterologous polypeptide expressed by the recombinant vector immunologically.

Next, this recombinant microorganisms can be administered to poultry for immunization whereafter it maintains itself for some time, or even replicates in th body of the inoculated animal, expressing in vivo a polypeptide coded for by the inserted nucleic acid sequence according to the invention resulting in the stimulation of the immune system of the inoculated animal. Suitable vectors for the incorporation of a nucleic acid sequence according to the invention can be derived from viruses such as pox viruses, e.g. vaccinia virus (EP 110,385, EP 83,286, U.S. Pat. No. 4,769,330 and U.S. Pat. No. 4,722 848) or fowl pox virus (WO 88/02022), herpes viruses such as HVT (WO 88/07088) or Marek's Disease virus, adeno virus or influenza virus, or bacteria such as *E. coli* or specific Salmonella species. With recombinant microorganisms of this type, the polypeptide synthesized in the host animal can be exposed as a surface antigen. In this context fusion of the polypeptide with OMP proteins, or pilus proteins of for example *E. coli* or synthetic provision of signal and anchor sequences which are recognized by the organism are conceivable. It is also possible that the Eimeria polypeptide, if desired as part of a larger whole, is released inside the animal to be immunized. In all of these cases it is also possible that one or more immunogenic products will find expression which generate protection against various pathogens and/or against various antigens of a given pathogen.

A vector vaccine according to the invention can be prepared by culturing a recombinant bacterium or a host cell infected with a recombinant vector comprising a nucleic acid sequence according to the invention, whereafter recombinant bacteria or vector containing cells and/or recombinant vector viruses grown in the cells can be collected, optionally in a pure form, and formed into a vaccine optionally in a lyophilised form.

Host cells transformed with a recombinant vector according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed into a vaccine, depending on its intended use. In order to purify the polypeptides produced, host cells transformed with a recombinant vector according to the invention are cultured in an adequate volume and the polypeptides produced are isolated from such cells, or from the medium if the protein is excreted. Polypeptides excreted into the medium can be isolated and purified by standard techniques, e.g. salt fractionation, centrifugation, ultrafiltration, chromatography, gel filtration or immuno affinity chromatography, whereas intra cellular polypeptides can be isolated by first collecting said cells, disrupting the cells, for example by sonication or by other mechanically disruptive means such as French press, followed by separation of the polypeptides from the other intracellular components and forming the polypeptides into a vaccine. Cell disruption could also be achieved by chemical (e.g. EDTA or detergents such as Triton X114) or enzymatic means, such as lysozyme digestion.

Antibodies or antiserum directed against a polypeptide according to the invention have a potential use in passive immunotherapy, diagnostic immunoassays and generation of anti-idiotypic antibodies.

The Eimeria proteins as characterized above can be used to produce antibodies, both polyclonal,monospecific and monoclonal. If polyclonal antibodies are desired, techniques for producing and processing polyclonal sera are known in the art (e.g. Mayer and Walter. eds, Immunochemical Methods in Cell and Molecular Biology, Academic Press, London, 1987). Monospecific antibodies to an immunogen can be affinity purified from polyspecific antisera by a modification of the method of Hall et al. (Nature, 311, 379–387, 1984). Monospecific antibody, as used herein, is defined as a single antibody species or multiple antibody species with homogeneous binding characteristics for the relevant antigen. Homogeneous binding, as used herein, refers to the ability of the antibody species to bind to a specific antigen or epitope.

Monoclonal antibodies, reactive against the Eimeria proteins according to the present invention, can be prepared by immunizing inbred mice by techniques known in the art (Kohler and Milstein, Nature, 256, 495–497, 1975). Hybridoma cells are selected by growth in hypoxanthine, thymidine and aminopterin in an appropriate cell culture medium such as Dulbecco's modified Eagle's medium. Antibody producing hybridomas are cloned, preferably using the soft agar technique of MacPherson, (Soft Agar Techniques, Tissue Culture Methods and Applications, Kruse and Paterson, eds., Academic Press, 276, 1973). Discrete colonies are transferred into individual wells of culture plates for cultivation in an appropriate culture medium. Antibody producing cells are identified by screening with the appropriate immunogen. Immunogen positive hybridoma cells are maintained by techniques known in the art. Specific antimonoclonal antibodies are produced by cultivating the hybridomas in vitro or preparing ascites fluid in mice following hybridoma injection by procedures known in the art.

Anti-idiotypic antibodies are immunoglobulins which carry an "internal image" of the antigen of the pathogen against which protection is desired and can be used as an immunogen in a vaccine (Dreesman et al., J. Infect. Disease, 151, 761, 1985). Techniques for raising anti-idiotypic antibodies are known in the art (MacNamara et al., Science, 226, 1325, 1984).

The vaccine according to the invention can be administered in a conventional active immunization scheme: single or repeated administration in a manner compatible with the dosage formulation, and in such amount as will be prophylactically effective, i.e. the amount of immunizing antigen or recombinant microorganism capable of expressing said antigen that will induce immunity in poultry against challenge by virulent Eimeria parasites. Immunity is defined as the induction of a significant level of protection in a population of chickens after vaccination compared to an unvaccinated group.

Next to an increase in protection a vaccine comprising the polypeptide of the invention will also reduce the number of oocysts shedded by the infected animals. Normally, the shedded oocysts will infect other animals in the flock. A decrease in the number of oocysts shedded will then also give a decrease in the number of animals which is subsequently infected and also a decrease in the number of oocysts shedded will give rise to a lesser infective load.

Furthermore, even without effect on the parasite itself, a vaccine can decrease the incidence of disease. This is especially so when the symptoms of the disease are caused by products released by the parasite. Vaccines directed against such products alleviate the symptoms without attacking the parasite.

For live viral vector vaccines the dose rate per chicken may range from 105–108 pfu. A typical subunit vaccine according to the invention comprises 1 µg–1 mg of the protein according to the invention. Such vaccines can be administered intradermally, subcutaneously, intramuscularly, intraperitoneally, intravenously, orally or intranasally.

Additionally the vaccine may also contain an aqueous medium or a water containing suspension, often mixed with other constituents in order to increase the activity and/or the shelf life. These constituents may be salts, pH buffers, stabilizers (such as skimmed milk or casein hydrolysate), emulsifiers, adjuvants to improve the immune response (e.g. oils, muramyl dipeptide, aluminium hydroxide, saponin, polyanions and amphipatic substances) and preservatives.

A vaccine comprising the polypeptide of the invention may also comprise other immunogenic proteins of *E. maxima* or immunogenic proteins of other Eimeria species. Such a combination vaccine will decrease the parasitic load in a flock of poultry and will increase the level of protection against coccidiosis.

It is clear that a vaccine according to the invention may also contain immunogens related to other pathogens of poultry, or may contain nucleic acid sequences encoding these immunogens, like antigens of Marek's Disease virus (MDV), Newcastle Disease virus (NDV), Infectious Bronchitis virus (IBV), Chicken Anemia Agent (CAA), Reo virus, Avian Retro virus, Fowl Adeno virus, Turkey Rhinotracheitis virus or *E. coli* to produce a multivalent vaccine.

The invention also relates to an "immunochemical reagent", which reagent comprises a protein according to the invention. The term "immunochemical reagent" signifies that the protein according to the invention is bound to a suitable support or is provided with a labelling substance.

The supports that may be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle.

Labelling substances which can be used are, inter alia, a radioactive isotope, a fluorescent compound, an enzyme, a dye sol, metal sol or metal compound as sol particle.

A nucleic acid sequence according to the invention can also be used to design specific probes for hybridization experiments for the detection of Eimeria related nucleic acids in any kind of tissue.

The present invention also comprises a test kit comprising said nucleic acid sequence useful for the diagnosis of Eimeria infection.

The invention also relates to a test kit to be used in an immunoassay, this test kit containing at least one immunochemical reagent according to the invention. The immunochemical reaction which takes place using this cest kit is preferably a sandwich reaction, an agglutination reaction, a competition reaction or an inhibition reaction.

For carrying out a sandwich reaction, the test kit can consist, for example, of a polypeptide according to the invention bonded to a solid support, for example the inner wall of a microtest well, and either a labelled polypeptide according to the invention or a labelled anti-antibody.

The invention is illustrated by the following examples.

EXAMPLE 1

Preparation of antigens of *E. maxima* sporozoites 1.a.i. Preparation of parasites

*Eimeria maxima* Houghton strain (*E. maxima* H) parasites were passaged through Light Sussex chickens as described by Long et al. (Folio Vet. Lat., 1976, 6: 201–207). Oocysts were isolated from faeces, sporulated in 2% potassium dichromate at 29° C. for 72 hours, surface sterilised by washing in 10% sodium hypochlorite and purified by flotation in saturated sodium chloride. Sporulated oocysts were suspended in phosphate buffered saline (PBS) pH 7.6 and broken by vibration. Sporocysts were suspended in PBS pH 7.6 containing 0.5% w/v porcine bile (Difco) and 0.25% w/v trypsin (Difco 1:250) and incubated at 41° C. for 30 minutes. Released sporozoites were washed in PBS pH 8.0, purified on columns of DE-52 (Whatman) as described by Schmatz et al. (J. Protozool., 1984, 31: 181–183) and stored as pellets in eppendorf tubes at −70° C.

1.a.ii. Preparation of antigens

Sporozoite pellets (5×107) were solubilised by boiling for 10 minutes in 100 ml of sample buffer (50 mM Tris-Cl pH 6.8, 2% SDS, 10% glycerol, 100 mM DTT and 10 mg/ml bromophenol blue) then loaded onto a discontinuous SDS-polyacrylamide gel. Gels were electrophoresed and polypeptides were transferred to nitrocellulose (NC) paper by the method of Towbin and Gordon (J. Immunol. Methods, 1984, 72: 313–340). After transfer, the NC paper was rinsed in PBS pH7.6 containing 0.3% Tween-20 and polypeptides were visualised by staining with colloidal gold (Aurodye, Cambio, England) according to the manufacturer's instructions.

The NC paper was cut into strips, each of which carried Eimeria polypeptides of a limited range of molecular mass. Each strip was cut into small pieces and the pieces transferred to labelled glass vials. To each vial, 400 ml of DMSO was added and the mixture left for 60 minutes to ensure solubilisation and sterilisation. NC particles were precipitated by the dropwise addition, with vigorous vortexing, of an equal volume of carbonate/bicarbonate buffer (50 mM, pH 9.6). Samples were transferred to 1.5 ml microcentrifuge tubes and centrifuged at 10,000 g for 5 minutes. NC particles were washed three times in RPMI 1640 medium (Gibco Biocult, Paisley, Scotland)), then finally suspended in 1 ml of this medium, divided into 200 ml aliquots, and stored frozen at −70° C.

EXAMPLE 2

Identification of lymphostimulatory antigens 2.a. Methods 2.a.i. Immunisation of animals For primary infections, groups of Reaseheath-C chickens (4 weeks old, 10 birds per group) were orally dosed with 4000 sporulated oocysts of E. maxima H. For secondary infections, the same birds were orally dosed with 50,000 sporulated oocysts of E. maxima H. For each experiment an age-matched control group of Reaseheath-C chickens were housed separately.

2.a.ii. Preparation of peripheral blood lymphocytes

Blood samples (5 ml) were withdrawn from superficial wing veins into plastic syringes containing heparin (10 units/ml). The blood was transferred to tubes (Falcon 2027, Becton-Dickinson) and centrifuged at 400 rpm for 15 minutes in a Sorvall RC3B centrifuge. The layer of cells above the sedimented erythrocytes was carefully removed by pipette into fresh tubes (Falcon 2059, Becton-Dickinson) and centrifuged at 2000 rpm for 10 minutes. The deposited cells were washed three times in RPMI 1640 containing 10% foetal calf serum (FCS, virus and mycoplasma screened, Gibco Biocult), 200 units/ml of penicillin and 200 mg/ml of streptomycin (G. R. Squibb & Sons, Moreton, England) and resuspended in the same medium at 4×106 cells/ml. 100 ml aliquots of cells (4×105) were pipetted into round bottomed wells of 96-well plates (Nunc-Gibco, Paisley, Scotland). To each well, 100 ml of a prepared sample was added. Test samples consisted of prepared NC particle suspensions (see Example 1.a.i) diluted in RPMI 1640 medium containing 10% FCS, 200 units/ml penicillin, 200 mg/ml streptomycin. To prepare dilutions, suspensions were thawed from −70° C., diluted ten-fold with medium and then a two-fold dilution series made. Control samples contained NC particle suspensions devoid of protein diluted identically. A second series of control samples contained a lysate of whole sporozoites (0.5 mg/ml of protein) prepared by freeze-thawing and sonicating sporozoites. Each sample was prepared in triplicate for each cell preparation with replicates placed randomly across plates. Plates were incubated for 96 hours at 41° C. in 5% CO2, pulsed for the final 16 hours with 1 mCi 3H-thymidine at 48 Ci/mMol (Amersham U.K.) then harvested (Dynatron Macromash Harvester, Dynatech Laboratories Ltd., Sussex, England) onto glass microfibre filters (MA781, Dynatron Laboratories Ltd.). After drying for 1 h at 50° C. the discs were placed in scintillation vials, 3.5 ml of liquid scintillation cocktail (Scintillator 299Tm Packard, Caversham, U.K.) was added and the radioactive incorporation measured in a scintillation spectrophotometer (Beckman Instruments Inc. LS9000).

2b. Results

Results are expressed as a stimulation index (SI) calculated for each sample with cells from each bird as follows:

$$SI = cpm1/cpm2$$

where:
cpm1=average counts per minute of triplicate cultures incubated with NC particles bearing protein.
cpm2=average counts per minute of triplicate cultures incubated with NC particles devoid of protein.

Solubilised NC strips containing polypeptides with relative molecular masses of approximately 73.000/71.000/69.000 D (collectively called 70.000 D) were found to stimulate the proliferation of lymphocytes from infected birds (see Table 1.). Lymphocytes from control birds were not stimulated to proliferate. The SIs varied from 4 to 9 and time-course studies showed that lymphocytes prepared from birds at 4 days after secondary infection proliferated most.

EXAMPLE 3

Raising and screening of antibodies to lymphostimulatory antigens 3.a. Methods 3.a.i. Immunisation of animals Pathogen-free rabbits (Harlan-Olac, Bicester, England) were maintained free of coccidia. Polypeptides of E. maxima H sporozoite pellets were solubilised, separated by SDS-polyacrylamide gel electrophoresis and transferred to NC as described in Example 1. NC strips bearing polypeptides with molecular masses of 70.000 D were excised, solubilised in DMSO as described in Example 1, washed in PBS pH 7.0 and finally suspended in 1 ml of PBS 7.0. Suspensions were injected subcutaneously into 4 sites (0.25 ml per site) and injections were repeated every 2 weeks using one NC strip per rabbit each time. Rabbits were bled 2 weeks after each injection.

3.a.ii. Screening of antisera by one and two dimensional blotting

Polypeptides of E. maxima H sporozoite pellets were solubilised and separated by SDS-polyacrylamide gel electrophoresis as described in Example 1. Alternatively, sporozoites (7×107) were suspended in 500 ml lysis buffer (0.2% Nonidet-P40, 20 mM CHAPS, 9M urea, 0.2% Biolytes 3–10 (Biorad), 1 mM DTT), sonicated (three ten-second bursts at 10 microns, MSE soniprep 50) and subjected to three cycles of freeze-thawing. Samples were centrifuged at 12,000 g in a microfuge for 1 minute then polypeptides separated by two-dimensional gel electrophoresis essentially as described by O'Farrell (J. Biol. Chem., 1975, 250: 4007–4021).

Separated polypeptides were transferred to NC paper as described in Example 1. The NC paper was immersed in TTN buffer (10 mM Tris-HCl pH 7.4, 500 mM NaCl, 0.05% Tween-20) containing 3% Bovine serum albumin (BSA) and incubated at room temperature, with gentle rocking, for 2 hours. The paper was rinsed in water, cut into strips and each strip incubated for 3 hours in a sample of rabbit serum diluted 1:250 in TTN containing 1% BSA. Strips were washed three times in TTN containing 0.5% Tween-20 then incubated for 1 hour in goat anti-rabbit IgG conjugated to alkaline phosphatase (Promega), diluted 1:7500 in TTN containing 1% BSA. Strips were washed a further three times in TTN containing 0.5% Tween-20 and once in AP buffer (100 mM Tris pH 9.5, 100 mM NaCl, 10 mM MgCl2). Binding of the phosphatase conjugate was detected by incubating strips in AP buffer containing 50 mg/ml nitroblue tetrazolium and 50 mg/ml bromochloroindolyl phosphate.

3.b. Results

The specificities of rabbit anti-p70 sera probed onto one-dimensional Western blots of polyeptides of *E. maxima* are shown in FIG. 1. Recognition of spots on two dimensional Western blots is summarised in Table 2.

EXAMPLE 4

Construction of an *E. maxima* sporozoite cDNA library 4.a. Methods 4.a.i. Isolation of mRNA

*E. maxima* sporozoites ($5 \times 10^8$) were purified as described in Example 1. Total cellular RNA was prepared using an RNA extraction kit (Pharmacia) according to the manufacturer's instructions. Briefly, sporozoites were lysed by incubation in buffered guanidinium thiocyanate, N-lauryl sarcosine and EDTA and RNA was separated from other cellular components by ultracentrifugation through buffered caesium trifluoroacetate. The RNA pellet was carefully dissolved in TE buffer (10 mM Tris-HCl pH 7.5, 1 mM EDTA) and stored at $-70°$ C. as an ethanol precipitate. Messenger RNA was purified from this total RNA preparation using columns of oligo (dT) cellulose (poly(A) Quik, Stragagene) according to the manufacturer's instructions.

4.a.ii. Synthesis and cloning of cDNA cDNA was synthesised from messenger RNA using a ZAP-cDNA™ synthesis kit (Stratagene) according to the manufacturer's instructions. The cDNA population ranged in size from less than 200 bp to around 6 kbp as judged by agarose gel electrophoresis and autoradiography of a small portion of the synthesised cDNA. The remaining cDNA was endrepaired using T4 DNA polymerase in the presence of all four dNTPs at 37° C. for 30 minutes. EcoRI adaptors were ligated onto the blunted ends of the cDNA using T4 DNA ligase at 8° C. for 24 hours. Digestion with XhoI produced cDNA with XhoI restriction sites at all 3' ends and EcoRI restriction sites at all 5' ends. Oligonucleotides (excess adaptors and the restriction enzyme digested primertemplate) were removed by centrifuging the sample through a 1 ml column of Sephacryl S-400.

100 ng portions of cDNA were ligated to 1 mg Uni-ZAP XR vector (Stratagene, digested with Eco RI and Xho I and dephosphorylated) overnight at 12° C. using T4 DNA ligase. Ligated DNA was packaged into phage heads using Gigapack II Gold packaging extract (Stratagene) according to the manufacturer's protocol. The resulting primary libraries were plated and amplified on *E. coli* SURE cells (Stratagene) and the resulting amplified libraries (Emx8 and Emx9) were titred on *E. coli* XL1-Blue cells (Stratagene) all according to manufacturer's instructions. Briefly, for all platings, host cells were grown overnight with shaking at 30° C. in L Broth supplemented with 0.2% (w/v) maltose and 10 mM MgSO4. Cells were diluted to OD600=0.5 with 10 mm MgSO4 before use. The number of recombinants in each library was determined by plating phage in the presence of 0.4% (w/v) 5-bromo-4-chloro-3-indolyl-β-D-galactoside (Xgal) and 2.5 mM isopropylthio-β-D-galactoside (IPTG) (Northumbria Biologicals Ltd.).

4.b. Results

Emx8 contains $3 \times 10^8$ pfu/ml (65% recombinant) and Emx9 contains $6 \times 10^8$ pfu/ml (55% recombinant)

EXAMPLE 5

Identification of cDNA clones coding for *E. maxima* p70 antigens.

5.a. Methods

Immunoscreening of cDNA libraries was done according to standard instructions supplied by Stratagene. The papers were immersed in rabbit anti-p70 serum diluted 1:100 in TTN containing 1% BSA. All further procedures were identical to those described for the development of Western blots in Example 3A. Positive plaques were identified and after storing overnight at +4° C. to elute bacteriophage particles, plaques were rescreened. Rescreening was continued until all the positives contained pure populations of antibody reactive plaques.

5.b. Results

Twenty independent plaques (pEm70/1 to pEm70/20) which reacted with rabbit anti-p70 serum were isolated and plaque purified from libraries Emx8 and Emx9.

EXAMPLE 6

Analysis of cDNA clones coding for *E. maxima* p70 antigens 6.a. Methods 6.a.i. Selection of clone-specific antibodies 0.2 ml aliquots of XL1-Blue cells were infected with $1-3 \times 10^3$ pfu from plaque purified phage populations. These were plated onto 90 mm dishes and treated according to the procedures described in Example 5.a. up to and including the overnight incubation of NC papers in TTN containing 3% BSA. Papers were then rinsed in TTN, each immersed in 5 ml rabbit anti-p70 serum diluted 1:100 in TTN containing 1% BSA and incubated with gentle rocking at room temperature for 6 hours. Papers were washed three times in TTN containing 3% BSA then bound antibody was eluted by immersing each paper in 5 ml 0.2M glycine pH 2.8 and rocking for 10 minutes. The eluant containing clone-specific antibodies was brought to neutral pH by the addition of 0.3M Tris, 10% (w/v) BSA. Clone specific antibodies were used undiluted to probe Western blots of *E. maxima* sporozoite proteins separated by one and two dimensional gel electrophoresis. All methods for the preparation and immunoscreening of Western blots are identical to those described in Example 3.a.ii.

6.a.ii. Analysis of cDNA inserts

DNA was prepared from stocks of recombinant phages using the method of Grossberger (Nucleic Acids Res., 1987, 15: 6737) and the cDNA inserts released by digestion with restriction enzymes Eco RI and Xho I. Each cDNA was ligated to pUC19 (Pharmacia) which had been digested with restriction enzymes Eco RI and Sal I and dephosphorylated with calf intestinal phosphatase. Ligated DNA was introduced into *E. coli* strain TG1 by transformation. Plasmids were isolated using the method of Choudhary (Nucleic Acids Res., 1991, 19: 2792) and analysed by digestion with restriction endonucleases.

As an alternative to subcloning into plasmid pUC19, cDNA clones were rescued into plasmid pbluescript by in vivo excision from recombinant lambda ZAPII according to instructions supplied by the manufacturer (Stratagene). pBluescript plasmids containing cDNA were isolated by alkaline lysis (Birnboim and Doly, 1979, Nucleic Acids Res., 7: 1513) and cDNAs analysed by digestion with restriction endonucleases.

6.a.iii. DNA sequence determination pEm70/1 was purified by equilibrium centrifugation in CsCl/ethidium bromide gradients and the cDNA insert was sequenced by random subcloning into M13 phage as described by Bankier and Barrell (Techniques in the Life Sciences (Biochemistry) 85: techniques in Nucleic Acids Biochemistry 1–34, 1983). For other clones, the 5' and 3' ends of the cDNA inserts were sequenced directly from double stranded plasmid DNA.

6.b. Results 6.b.i. Reactivity of clone-specific antibodies

Twenty plaque-purified lambda populations isolated from libraries Emx8 and Emx9 (see example 5) were used to produce clone-specific antibodies. Fourteen of these antibodies specifically cross-reacted with polypeptides of around 70 kDa on one-dimensional blots of *E. maxima* sporozoite proteins. The clone-selected antibodies were used to probe two dimensional blots of *E. maxima* sporozoite proteins. Polypeptide spots were identified by arbitrary numbering and the five clone-selected antibodies reacted with constellations of spots which were sub-sets of the spots recognised by intact rabbit anti-p70 serum. This information is summarised in Table 2.

6.b.ii. Restriction mapping

Analytical restriction enzyme digestions of the fourteen clones that selected antibodies specific for 70 kDa polypeptides showed there were six differently sized cDNA inserts. Two of these were called pEm70/1 and pEm70/4. Restriction enzyme maps of the two cDNA inserts are shown in FIG. 2.

6.b.iii. Analysis of DNA sequences

The nucleotide sequence found is of pEm70/1 and its deduced amino acid sequence is shown in SEQ. ID. NO. 1 from nucleic acid 126. The sequence found in clone pEm70/1 is a 1294 bp cDNA including the 5' EcoRI adaptor and a 3' polyA sequence followed by an XhoI site. The cDNA appears to be "open" from the first triplet of nucleotides to an ochre termination codon (TAA) at 1258 bp which precedes the poly(A) sequence. The deduced amino acid sequence encodes a protein of 419 amino acids or approximately 46 kilodaltons. The cDNA has internal EcoRI sites at 67 bp and 1000 bp and unique ScaI (699 bp), HindIII (736 bp), SspI (995 bp), HincII (1200 bp) and PstI (1251 bp) restriction sites (basepairs measured in distance from start of the sequence found in clone pEm70/1, i.e. nucleic acid 126 in SEQ ID NO:1). The analysis of the first 125 nucleotides of the sequence shown in SEQ ID NO:1 is discussed in Example 9.

The 5' and 3' end sequences of pEm70/4 are shown in SEQ. ID. NOS. 3 and 5.

EXAMPLE 7

Expression of the recombinant protein encoded by pEm70/1

7.a. Methods 7.a.i Construction of plasmid pRSETAEm70/1

1 μg of plasmid pEm70/1 was digested with 10 units of BamHI and 10 units of XhoI for 2 hours at 37° C. and the cDNA insert ligated into BamHI-XhoI digested and dephosphorylated plasmid pRSETA (InVitrogen). Ligated DNA was transfected into *E. coli* strain HMS174, colonies containing recombinant plasmid pRSETAEm70/1 were picked and plasmid DNA was isolated by alkaline lysis (Birnboim and Doly, Nucl. Acid. Res., 7, 1513, 1979).

7.a.ii Expression of (His)6-Em70/1 fusion protein from plasmid pRSETAEm70/1.

Bacteria harbouring plasmid were grown overnight in L-broth containing 100 μg/ml ampicillin. 10 ml of overnight culture were diluted 1:100 in prewarmed (37° C.) L-broth and grown with aeration for 5 hours at 37° C. Samples were removed for Western blot analysis.

7.a.iii Purification of (His)6-Em70/1 fusion protein by metal-affinity chromatography.

The 5 hour culture of pRSETAEm70/1 was centrifuged and the bacterial pellet resuspended in 5 ml, 6M guanidine-HCl, 20 mM sodium phosphate pH 7.8 and sonicated for four bursts of thirty seconds on full power (MSE Soniprep). The sonicate was centrifuged at 10,000× g to remove insoluble material and the supernate mixed with 10 ml immobilised nickel resin ("ProBondTM", InVitrogen) which had been equilibrated in 8M urea, 20 mM sodium phosphate pH7.8. The resin and lysate mixture was poured into a glass column and the resin allowed to settle for 30 minutes. A tap at the bottom of the column was opened and the "flow through" was collected, re-applied to the resin and collected. The resin was washed with equilibration buffer until the eluate had an absorbance <0.05 at 280 nm (A280). The resin was washed with equilibration buffer at pH6.0 to remove non-specifically bound bacterial proteins and the recombinant protein was finally eluted with equilibration buffer at pH4.0. The recombinant protein was dialysed for 16 hours at +4° C. against a large volume of PBS pH7.6. The concentration of protein was estimated using a dye binding reagent (Bio-Rad), the yield was approximately 5 mg from 1 litre culture.

7.b. Results

Figure 3:
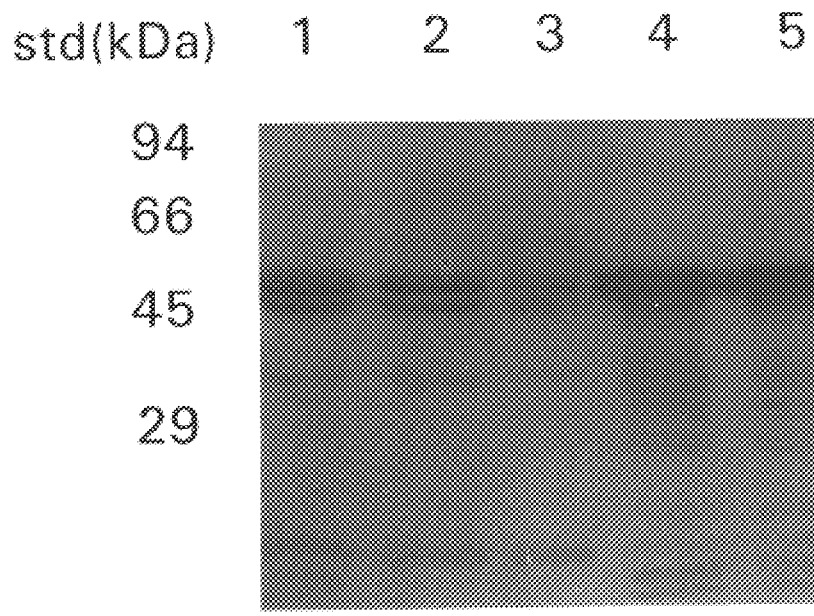
FIG. 3 shows a Western blot of purified pEm 70/1 protein probed with chicken anti-recombinant pEm 70/1 serum.
Figure 4:
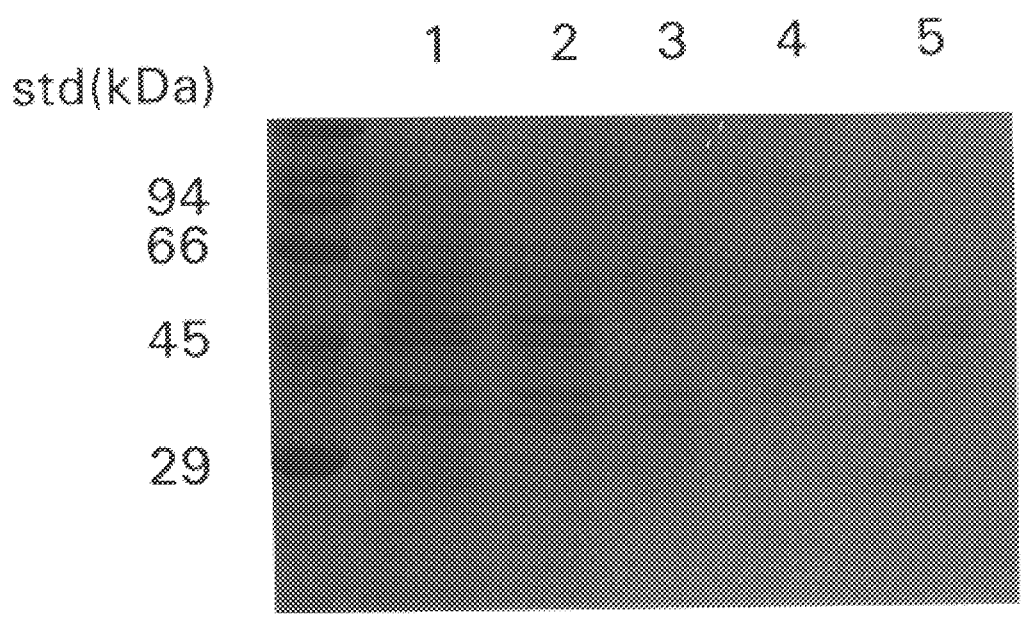
FIG. 4 is an SDS-PAGE of the purification of recombinant pEm 70/1.

Recombinant pEm70/1 was expressed in *E. coli* as a fusion with six histidine residues at its N-terminus. The fusion protein that reacted specifically with rabbit anti-p70 or with chicken anti-recombinant pEm70/1 sera was a doublet of 46–48 kDa (FIG. 3, track 1). The contribution of protein from the expression vector is six histidines and the enterokinase recognition sequence (asp-asp-asp-lys) which totals around 1 kDa. The recombinant protein produced in the 5 hour culture (FIG. 3, track 1) was present in the soluble fraction after sonication (FIG. 3, track 2) and was purified from the nickel affinity column (FIG. 3, tracks 4 and 5). FIG. 4 shows the Coomassie stained polyacrylamide gel of the purification of the recombinant protein expressed by pRSETAEm70/1.

EXAMPLE 8

Immunisation of chickens with the recombinant protein (His)6-Em70/1.

8.a. Methods 8.a.i Immunisation of animals.

Thirty six Light Sussex birds were reared under coccidia-free conditions until three weeks of age. Birds were randomly assigned to two groups and were housed individually in single bird cages. Samples of blood were taken and eighteen birds were immunised by sub-cutaneous injection (0.1 ml) of 25 μg antigen (prepared as described in Example 7) and 100 μg saponin in PBS. The remaining eighteen birds were immunised with 25 μg bacterial antigen (that did not bind to the nickel resin) and 5 μg saponin in PBS. Immunisations were repeated twice more at two weekly intervals and blood samples were taken following each immunisation.

8.a.ii Challenge of animals.

Two weeks after the final immunisation, all birds were given 100 sporulated oocysts of *E. maxima* by oral intubation. The faeces of each bird were harvested by daily collections onto papered trays and the total number of oocysts excreted by each bird from 5 to 10 days postchallenge was calculated by counting mixed and diluted samples of faeces in Macmaster counting chambers.

8.b. Results

Table 3 shows the individual oocyst output and group means of the two groups of birds either immunised with antigen or mock-immunised. Birds which received antigen had oocyst outputs lower than the mock-immunised group indicating that the antigen, as described in Example 7, can be used to protect chickens against infections with *Eimeria maxima*.

EXAMPLE 9

Additional 5' nucleotide sequence of the Em70/1 gene.

9.a. Methods

The 5' RACE (rapid amplification of cDNA ends) technique (Frohman et al., Proc. Natl. Acad. Sci., 85, 8998, 1988; Belyavsky et al. Nucl. Acids Res., 17, 2919, 1988; CLONTECH laboratories) was used to obtain more of the 5' DNA sequence of the gene encoding the cDNA Em70/1. Messenger RNA was isolated from 200×106 *E. maxima* sporozoites using a Fasttrack kit (InVitrogen). cDNA was synthesized from 2 µg mRNA using AMV reverse transcriptase according to the manufacturer's instructions (CLONTACH Laboratories Inc) except that 1 µg of random primers was used to prime first strand cDNA synthesis instead of a gene specific primer. RNA was hydrolysed with NaOH and an anchor primer (SEQ ID NO:6) was ligated to the 5' end of the cDNA using RNA ligase. The ligated cDNA was diluted 1:10 with water and then analysed by PCR (polymerase chain reaction) using an anchor specific primer (SEQ ID NO:7) and an antisense gene-specific primer (SEQ ID NO:8). PCR gave a single product of approximately 800 bp as judged by agarose gel electrophoresis. This fragment was excised from the agarose gel using a GeneClean kit (Stratatech Scientific), digested with 10 units EcoRI and ligated to EcoRI-digested and dephosphorylated M13mp18. After transfection into *E. coli* strain TG1, recombinant plaques were picked, single stranded DNA was isolated and the nucleotide sequence of inserts determined using the PRISMTM DyeDeoxyTM Terminator Cycle Sequencing Kit (Applied Biosystems).

9.b. Results

Using the 5' RACE followed by EcoRI sub-cloning, an additional 125 nucleotides upstream Em70/1 which linked up with the previously (Example 6) determined sequence were obtained.

EXAMPLE 10

Expression of the *E. maxima* Em70/1 antigen in insect cells using baculovirus as vector.

10.a. Construction of pAcEM

The XhoI site of pEm70/1 was converted into BglII by means of a synthetic linker using the methodology as described by Sambrook, J. et al. (Molecular Cloning, A laboratory Manual, Chapter 8). The 1.3 kb insert of pEm70/1 containing the gene encoding antigen 70/1 was subsequently isolated as a BamHI-BglII fragment and ligated into the BamHI site of the baculo transfer vector pAcLacZ+MCS obtained from Dr. D. Bishop, Institute of Virology, Oxford, U.K.

Correct integration relative to the polyhedrin promoter was verified by restriction digests.

From previous sequence analyses it was known that the coding region of the insert of pEm70/1 was incomplete at the N-terminus and was lacking an ATG-initiator.

In order to allow expression, a 42 bp synthetic DNA fragment composed of the complementary oligos L1 (SEQ ID no. 9) and L2 (SEQ ID no. 10) with BamHI compatible protruding ends, was ligated into the unique BamHI site that was restored after insertion of the 1.3 kb fragment from pEm70/1 into pAcLacZ+MCS. This resulted in plasmid pAcEM. The correctly inserted 42 bp linker in pAcEM provided a reading frame of the first 11 amino acids of the polyhedrin protein fused to the *E. maxima* gene encoding a major part of antigen 70/1. The final structure downstream of the polyhedrin promoter in plasmid pAcEM was verified by nucleotide sequencing.

10.b. Transfection of insect cells and isolation of baculovirus recombinants.

pAcEM DNA was transfected into Sf9 cells using standard techniques (D. O'Reilly, K. Miller, and V. Luckow: Baculovirus expression vectors, a laboratory manual, Oxford University press, 1994), using Lipofectin (Gibco/BRL) and wildtype baculovirus DNA. Recombinant plaques were identified on tissue-culture dishes with X-gal (Gibco/BRL) in the agar-overlay. Blue plaques were picked and replated three times, till no wildtype virus was detectable. The viral plaque was amplified in T75 and T175 flasks and finally in a 100 ml spinnerbottle with SF9 cells. The viral titre was determined by way of immunofluorescence: microtitre plates with Sf9 cells were infected with a dilution of the virus. After 6 days of incubation the plates were fixed with alcohol, and stained with a 1:500 dilution of a chicken polyclonal antibody raised against the Em70/1 sporozoite protein. Next incubation was with 1:600 Goat-anti-chicken IgG (KPL)-conjugated to FITC. The titre of the stock of vAcEM virus was 7.2 Log10 TCID50/ml.

10.c. Production of *E. maxima* 70/1 protein in insect cells.

Four T175 flasks each containing 3×107 Sf9 cells in exponential growth were infected with the vAcEM virus stock at an moi of 10 TCID50/cell. After three days the infected cells were harvested on ice. The cells were resuspended at 1×107/ml in PBS and sonicated. The sonicates were inactivated with 0.075% formalin, by incubating at 4° C. for 1 week. Formaldehyde was neutralized with an equimolar amount of Na2S205.

10.d. Analysis of baculo-expressed product using SDS-PAGE and Western Blotting.

Samples of resuspended cells after sonication were mixed 2:3 with reduced (R) or non-reduced (NR) sample buffer (consisting of 188 mM Tris-HCl pH6.8, 6% SDS±0.2M β-mercapto-ethanol), boiled for 10 min. at 95° C., centrifuged for 10 min at 13000 rpm and loaded onto SDS-gels. Uninfected cells and SHAM-recombinant infected cells without insert were included as controls.

Samples were analysed on 12% PAA gel (1.5 mm thick). In each lane 80 µl sample was loaded. Part of the gel was stained with CBB (Coommassie Brilliant Blue R250), the rest was electro-blotted onto nitrocellulose.

Blot was incubated with chickenserum raised against *E. max* 70/1 sporozoite protein diluted 1:500 (or negative chicken serum as control). Both blots were developed with alkaline phosphatase-labelled goat anti-chicken IgG and the NBT/BCIP substrate according to standard protocols.

Only the Em70/1 containing virus expressed a band recognised by the chicken serum. The approximate Mr of the expressed product was 45,000, with a break-down product visible at Mr 33,000. No difference was detectable in expression and recognition after running the gel under reducing or non-reducing conditions.

EXAMPLE 11

Immunisation of chickens with *Salmonella gallinarum*-Em70/1

11.a. Methods

Figure 5:
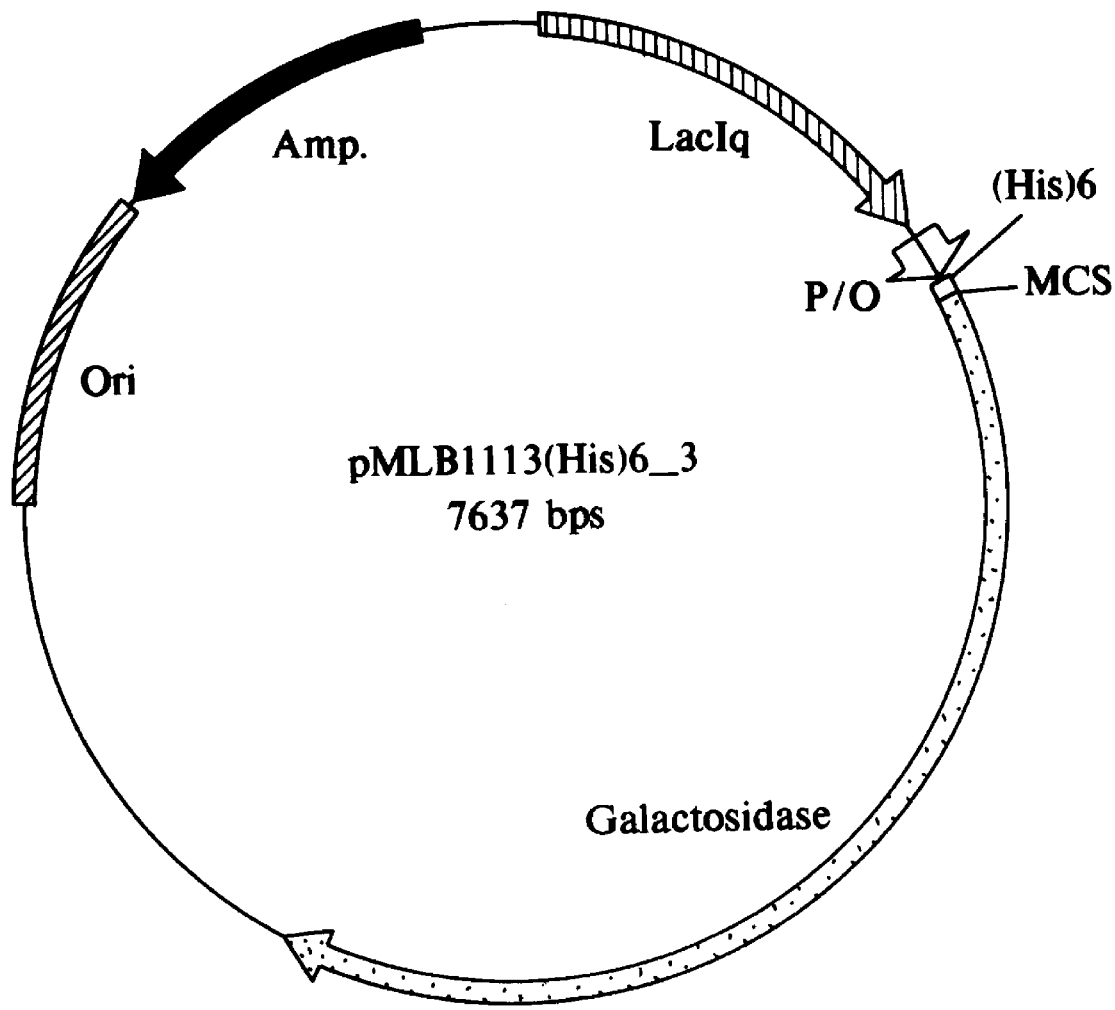
FIG. 5 is the genetic map of pMLB1113(His)6-3.

2 μg of purified plasmid pEm70/1 was cloned into the MCS (multiple cloning site) of pMLB1113(His)6_3 vector (see FIG. 5.) after digestion with EcoRI (20 units). The ligated DNA was used to transform *E. coli* TG1. Recombinant colonies were selected on L-agar plates containing 100 μg ampicillin and plasmids prepared by alkaline lysis (Birnboim & Doly). Plasmids were analysed by restriction enzyme digestion and agarose gel electrophoresis and a single recombinant plasmid pMLB(His)6_3-Em70/1, containing the 932 bp EcoRI fragment in the right orientation was selected.

*Salmonella gallinarum* 9R strain (H. Williams Smith, J. Hygiene, 54, 419, 1956) was transformed with plasmid pMLB1113(His)6_3-Em70/1 using the high effiency protocol of Hanahan (J. Mol. Biol. 166, 557, 1983). One plaque purified recombinant colony was cultured, with aeration, in 50 ml L-broth+50 μg ampicillin at 37° C. and grown to a density of 108 bacteria/ml.

The bacteria were concentrated and washed by centrifugation for 10 min at 4000 g at 4° C. and diluted with L-broth to the immunising concentration being 109/ml.

Twelve 3 wk old White-Leghorn chickens were injected with 108 Salmonella 9R-Em70/1 in 0.1 ml L-broth given intramuscularly. This vaccination was repeated twice with two week intervals. Salmonella 9R parent strain was processed similarly and given in the same dose to control chickens. All chickens were challenged at two weeks after the final vaccination. Challenge and assessment of protection was performed as described in example 8.a.ii.

11.b. Results

The reduction in mean oocyst output of both groups is given in Table 4.

Birds which received the Salmonella vector vaccine had on average lower oocyst outputs compared to their controls. This indicates that this vector vaccine could be used to reduce the parasite burden of vaccinated animals and thereby the pathogenic effects associated with the infection.

TABLE 1

Stimulation Indices of Immune and Control birds exposed to nitrocellulose-bourne antigents of E. maxima sporozoites. Each S.I. is the mean of ten individual birds.

| Strip number (Mr) | Experiment 1 Immune birds | Experiment 2 Immune birds | Experiment 1 Control birds | Experiment 2 Control birds |
|---|---|---|---|---|
| 6 (73k) | 3.12 | 2.60 | 1.11 | 1.04 |
| 7 (71k) | 2.60 | 1.97 | 1.39 | 1.16 |
| 8 (69k) | 5.57 | 4.76 | 0.99 | 1.64 |

TABLE 2

2-D gel analysis of E. maxima H sporozoites - indentification of spots which are lymphostimulatory, recognised by rabbit anti-70kDa serum or recognized by clone-specific antibodies.

| Spot no. | anti-70 kDa sera | Clone 12 pEM70/1 | lympho-stimulatory |
|---|---|---|---|
| 5 | + | | |
| 6 | + | + | |
| 7 | + | | |
| 10 | + | | |
| 13 | + | | + |
| 22 | + | + | |
| 23 | + | + | + |
| 41 | + | + | |
| 42 | + | + | |
| 43 | + | + | |
| 48 | + | + | + |
| 52 | + | | |
| 54 | + | + | |
| 56 | + | | |

TABLE 3

In vivo protection against challange infection with E. maxima: Oocyst outputs of birds immunised with fusion protein pRSETAEm70/1 (group 1) compared to mock-immunised birds (group 2).

| Group | Bird No. | Oocyst output ($\times 10^6$) | mean | SD |
|---|---|---|---|---|
| 1 | 1 | 37.9 | 33.4 | 14.8 |
| | 3 | 50.5 | | |
| | 4 | 30.0 | | |
| | 5 | 12.4 | | |
| | 6 | 44.2 | | |
| | 7 | 48.5 | | |
| | 8 | 28.1 | | |
| | 9 | 37.9 | | |
| | 10 | 46.7 | | |
| | 11 | 42.9 | | |
| | 12 | 27.2 | | |
| | 13 | 36.8 | | |
| | 14 | 22.6 | | |
| | 15 | 61.3 | | |
| | 16 | 12.0 | | |
| | 17 | 14.0 | | |
| | 18 | 15.6 | | |
| 2 | 19 | 33.3 | 40.4 | 12.7 |
| | 20 | 36.8 | | |
| | 21 | 18.8 | | |
| | 22 | 36.5 | | |
| | 23 | 48.2 | | |
| | 24 | 30.3 | | |
| | 25 | 48.6 | | |
| | 26 | 29.4 | | |
| | 27 | 32.5 | | |
| | 28 | 43.5 | | |
| | 29 | 48.0 | | |
| | 30 | 41.0 | | |
| | 31 | 20.4 | | |
| | 32 | 41.6 | | |
| | 33 | 39.0 | | |
| | 34 | 49.9 | | |
| | 35 | 61.0 | | |
| | 36 | 68.9 | | |

TABLE 4

| Mean E. maxima oocyst output of chickens vaccinated with S. gallinarum-Em70/1 | |
|---|---|
| Treatment | Oocyst output [×10−6] |
| S. gallinarum-Em70-1 | 34.0 ± 9 |
| S. gallinarum 9R control | 41.3 ± 13 |

We claim:

1. A nucleic acid molecule that codes for a protein that has a sequence selected from the croup consisting of SEQ ID NO:2, SEQ ID NO:4 and portions of SEQ ID NO:2 and SEQ ID NO:4 that comprise an epitope that will bind to antibodies in antiserum raised against either of the peptides of SEQ ID NO:2 and SEQ ID NO:4.

2. A nucleic acid molecule according to claim 1 wherein the nucleic acid molecule contains at least part of the DNA sequence shown in SEQ ID No. 3.

3. A recombinant nucleic acid molecule comprising a nucleic acid molecule according to claim 1 operatively linked to expression control sequences enabling expression of said nucleic acid molecule.

4. A recombinant vector comprising a nucleic acid molecule according to claim 1.

5. A recombinant vector according to claim 4 wherein the nucleic acid molecule is operatively linked to expression control sequences.

6. A host cell or organism transformed with a recombinant vector molecule according to claim 4.

7. A process for expression of an Eimeria protein, comprising culturing a host cell according to claim 6.

8. A host cell or organism transformed with a nucleic acid molecule according to claim 1.

9. A process for expressing an Eimeria protein comprising culturing a host cell according to claim 8.

10. A nucleic acid molecule according to claim 1 wherein the nucleic acid molecule contains the DNA sequence shown in SEQ ID No. 1 or a portion thereof that codes for an epitope that will bind to antibodies of antisera raised against the protein that is coded for by SEQ ID NO:1.

11. A recombinant nucleic acid molecule comprising a nucleic acid molecule according to claim 10 operatively linked to expression control sequences enabling expression of said nucleic acid molecule.

12. A recombinant vector comprising a nucleic acid molecule according to claim 10.

13. A recombinant vector according to claim 12, wherein the nucleic acid molecule is operatively linked to expression control sequences.

14. A host cell or organism transformed with a recombinant vector according to claim 12.

15. A process for expression of an Eimeria protein comprising culturing a host cell according to claim 14.

16. A host cell or organism transformed with a nucleic acid molecule according to claim 10.

17. A process for expressing an Eimeria protein comprising culturing a host cell according to claim 16.

* * * * *